United States Patent
Mansergh et al.

(10) Patent No.: US 10,866,208 B2
(45) Date of Patent: Dec. 15, 2020

(54) EXTENSIBLE, MULTIMODAL SENSOR FUSION PLATFORM FOR REMOTE, PROXIMAL TERRAIN SENSING

(71) Applicant: Teralytic, Inc., New York, NY (US)

(72) Inventors: Ryan Mansergh, San Francisco, CA (US); Steven Ridder, New York, NY (US); Elliott Highfill, New York, NY (US)

(73) Assignee: Teralytic, Inc., New York, NY (US)

( * ) Notice: Subject to any disclaimer, the term of this patent is extended or adjusted under 35 U.S.C. 154(b) by 0 days.

(21) Appl. No.: 16/578,184

(22) Filed: Sep. 20, 2019

(65) Prior Publication Data

US 2020/0096474 A1 Mar. 26, 2020

Related U.S. Application Data

(60) Provisional application No. 62/734,639, filed on Sep. 21, 2018.

(51) Int. Cl.
*G01N 27/414* (2006.01)
*G01K 13/00* (2006.01)
(Continued)

(52) U.S. Cl.
CPC ........... *G01N 27/414* (2013.01); *G01K 13/00* (2013.01); *G01N 27/041* (2013.01); *G01N 27/27* (2013.01);
(Continued)

(58) Field of Classification Search
CPC .......................... G01N 2033/245; G01N 27/27
See application file for complete search history.

(56) References Cited

U.S. PATENT DOCUMENTS

| 4,273,636 A | 6/1981 | Shimada et al. |
| 4,502,938 A | 3/1985 | Convington et al. |

(Continued)

FOREIGN PATENT DOCUMENTS

| JP | H10-14402 A | 1/1998 | |
| WO | WO-2009157755 A2 * | 12/2009 | ............. G01N 33/24 |
| WO | WO 2011/127905 A1 | 10/2011 | |

OTHER PUBLICATIONS

International Search Report and Written Opinion dated Mar. 19, 2020 for International Application No. PCT/US2019/052247, 17 pages.

(Continued)

*Primary Examiner* — Daniel S Larkin
(74) *Attorney, Agent, or Firm* — Cooley LLP

(57) ABSTRACT

A sensor assembly includes a housing and multiple sensor array segments. A first sensor array segment includes an antenna. A second sensor array segment has a soil temperature sensor, an electrical conductivity (EC) sensor, a moisture sensor, an ion-sensitive field effect transistor (ISFET) nitrate sensor for detecting nitrates in adjacent soil, an ISFET phosphate sensor for detecting phosphates in adjacent soil, an ISFET potassium sensor for detecting potassium in adjacent soil, and an ISFET pH sensor for detecting pH in adjacent soil, and a reference electrode electrically coupled to the first sensor array segment and to the second sensor array segment. The first sensor array segment and the reference electrode can be disposed on opposite sides of the second sensor array segment.

11 Claims, 31 Drawing Sheets

(51) Int. Cl.
*G01N 27/04* (2006.01)
*G01N 27/27* (2006.01)
*G01N 33/24* (2006.01)
(52) U.S. Cl.
CPC ..... *G01N 33/246* (2013.01); *G01N 2033/245* (2013.01)

(56) References Cited

U.S. PATENT DOCUMENTS

| | | | |
|---|---|---|---|
| 4,567,563 A * | 1/1986 | Hirsch | A01G 25/16 700/284 |
| 4,701,253 A | 10/1987 | Ligtenberg et al. | |
| 4,772,377 A | 9/1988 | Geist et al. | |
| 4,908,117 A | 3/1990 | Kinlen et al. | |
| 4,966,678 A | 10/1990 | Moore et al. | |
| 5,911,873 A | 6/1999 | McCarron et al. | |
| 6,232,786 B1 | 5/2001 | Barnett | |
| 7,309,621 B2 | 12/2007 | Conley, Jr. et al. | |
| 7,318,887 B2 | 1/2008 | Rhodes | |
| 7,587,297 B2 * | 9/2009 | Glenn | G06Q 30/02 47/1.7 |
| 7,927,883 B2 | 4/2011 | Tuli et al. | |
| 8,444,937 B2 | 5/2013 | Tuli et al. | |
| 8,702,964 B2 | 4/2014 | Ahmad | |
| 9,281,219 B2 | 3/2016 | Stimpson et al. | |
| 9,500,614 B2 | 11/2016 | Press et al. | |
| 9,535,031 B2 | 1/2017 | Stimpson et al. | |
| 2009/0322357 A1 * | 12/2009 | Beaulieu | G01V 3/088 324/692 |
| 2010/0137143 A1 | 6/2010 | Rothberg et al. | |
| 2012/0001646 A1 | 1/2012 | Bolander et al. | |
| 2013/0226347 A1 * | 8/2013 | Martinez | A01C 21/007 700/266 |
| 2014/0348707 A1 | 11/2014 | King Smith et al. | |
| 2015/0168594 A1 * | 6/2015 | Chang | G01V 9/00 73/866 |
| 2016/0077042 A1 | 3/2016 | Warwick et al. | |
| 2016/0157446 A1 | 6/2016 | Bentwich | |
| 2016/0327511 A1 | 11/2016 | Wenzel et al. | |
| 2017/0322179 A1 * | 11/2017 | Alonso Chamarro | G01N 33/24 |
| 2018/0279536 A1 * | 10/2018 | Bindhammer | A01B 79/005 |
| 2019/0128865 A1 * | 5/2019 | Basu | H04Q 9/00 |
| 2019/0324168 A1 * | 10/2019 | Kiss | G01N 33/24 |

OTHER PUBLICATIONS

Aboukila, E. F. & Norton, J. B., "Estimation of Saturated Soil Paste Salinity From Soil-Water Extracts," Soil Sci, 182:107-113(2017).
Abramova, N. & Bratov, A., "Photocurable Polymers for Ion Selective Field Effect Transistors. 20 Years of Applications," Sensors, 9:7097-7110 (2009); doi:10.3390/s90907097.
Adamchuk, V. I. et al., "Feasibility of On-the-go Mapping of Soil Nitrate and Potassium Using Ion-Selective Electrodes," 2002 ASAE Annual International Meeting, Presentation Paper No. 02-1183, Chicago, Illinois, Jul. 28-Jul. 31, 2002.
Adamchuk, V. I. et al., "On-the-go soil sensors for precision agriculture," Computers and Electronics in Agriculture, 44:71-91 (2004).
Adamchuk, V. I. et al., "Direct measurement of soil chemical properties on-the-go using ion-selective electrodes," Computers and Electronics in Agriculture, 48:272-294 (2005).
Adamchuk, V. I. et al., "Evaluation of an on-the-go technology for soil pH mapping," Precision Agric, 8:139-149 (2007).
Ahlborn, K. et al., "PLD as a new technology for the fabrication of pH glass based planar electrochemical sensors," International Journal on Advances in Systems and Measurements, 10(1-2):56-63 (2017); http://www.iariajournals.org/systems_and_measurements/.
Alegret, S. et al., "pH-ISFET with NMOS Technology," Electroanalysis, 3:355-360 (1991).

Ali, M. B. et al., "Sensitive cyclodextrin-polysiloxane gel membranes on EIS structure and ISFET for heavy metal ion detection," Sensors and Actuators B, 62:233-237 (2000).
Alonso, J. et al., "Analysis and identification of several apple varieties using ISFETs sensors," Talanta, 59:1245-1252 (2003).
Amente, G. et al., "Estimation of Soil Solution Electrical Conductivity from Bulk Soil Electrical Conductivity in Sandy Soils," Soil Sci. Soc. Am. J., 64:1931-1939 (2000).
An, H., "Bis- and Oligo(benzocrown ether)s," Chem. Rev., 94:939-991 (1994).
Andersen, H. E. et al., "Leaching of dissolved phosphorous from tile-drained agricultural areas," Water Science & Technology, 73(12):2953-2958 (2016).
Antonisse, M. M. G. et al., "Nitrate and Bicarbonate Selective CHEMFETS," Proceedings of the International Solid-State Sensors and Actuators Conference—Transducers '95, 1:867-869 (1995).
Antonisse, M. M. G. et al., "Durable nitrate-selective chemically modified field effect transistors based on new polysiloxane membranes," Analytica Chimica Acta, 332:123-129 (1996).
Antonisse, M. M. G. et al., "Neutral Anion Receptors: Synthesis and Evaluation as Sensing Molecules in Chemically Modified Field Effect Transistors," J. Org. Chem., 62:9034-9038 (1997).
Antonisse, M. M. G. et al., "$H_2PO_4$-selective CHEMFETs with uranyl salophene receptors," Sensors and Actuators B, 47:9-12 (1998).
Antonisse, M. M. G. et al., "Membrane Characterization of Anion-Selective CHEMFETs by Impedance Spectroscopy," Anal. Chem., 72:343-348 (2000).
Arauzo, M. et al., "Field evaluation of Gee Passive Capillary Lysimeters for monitoring drainage in non-gravelly and gravelly alluvial soils: A useful tool to estimate nitrogen leaching from agriculture," Agriculture Water Management, 97:465-474 (2010).
Arshak, K. et al., "A review of gas sensors employed in electronic nose applications," Sensor Review, 24(2):181-198 (2004).
Artigas, J. et al., "Application of ion sensitive field effect transistor based sensors to soil analysis," Computers and Electronics in Agriculture, 31:281-293 (2001).
Artigas, J. et al., "Development of a photopolymerisable membrane for calcium ion sensors Application to soil drainage waters," Analytica Chimica Acta, 426:3-10 (2001).
Artigas, J. et al., "Development of a screen-printed thick-film nitrate sensor based on a graphite-epoxy composite for agricultural applications," Sensors and Actuators B, 88:337-344 (2003).
Bakker, E. et al., "Carrier-Based Ion-Selective Electrodes and Bulk Optodes. 1. General Characteristics," Chem. Rev., 97:3083-3132 (1997).
Bamsey, M. et al., "Ion-Specific Nutrient Management in Closed Systems: The Necessity for Ion-Selective Sensors in Terrestrial and Space-Based Agriculture and Water Management Systems," Sensors, 12:13349-13392 (2012); doi:10-3390/s121013349.
Bargavi, K. & Aiyappan, S., "Analysis of nutrient content in the soil using ISFET via GSM for agricultural development in rural India," International Journal of Advanced Research in Computer Science and Electronics Engineering (IJARCSEE), 3(7):375-379 (2013).
Barhoumi, L. et al., "Silicon Nitride Capacitive Chemical Sensor for Phosphate Ion Detection Based on Copper Phthalocyanine—Acrylate-Polymer," Electroanalysis, 29 (2017), 11 pages; doi:10-1002/elan.201700005.
Barnes, E. M. et al., "Remote- and Ground-Based Sensor Techniques to Map Soil Properties," Photogrammetric Engineering & Remote Sensing, 69(6):619-630 (2003).
Bataillard, P. et al., "The preparation of CHEMFET selective gates by thin silica layer grafting and their behaviour," Sensors and Actuators, 12:245-254 (1987).
Bausells, J. et al., "Ion-sensitive field-effect transistors fabricated in a commercial CMOS technology," Sensors and Actuators B, 57:56-62 (1999).
Bedner, K. & Rumänien, "Fabrication and Characterization of Ion-Sensitive Field-Effect Transistors using Silicon-on-Insulator Technology," Thesis, Apr. 23, 2013, 107 pages.
Belter, M. et al., "Over a century of detection and quantification capabilities in analytical chemistry—Historical overview and trends," Talanta, 129:606-616 (2014).

(56) References Cited

OTHER PUBLICATIONS

Beltran, A. et al., "Development of Durable Nitrate-Selective Membranes for All-Solid State ISE and ISFET Sensors Based on Photocurable Compositions," Electroanalysis, 14(3):213-220 (2002).
Ben-Dor, E. et al., "Imaging spectrometry for Soil Applications," Advances in Agronomy, 97:321-392 (2008).
Bergveld, P., "The Operation of an ISFET as an Electronic Device," Sensors and Actuators, 1:17-29 (1981).
Bergveld, P. et al., "How Electrical and Chemical Requirements for REFETs May Coincide," Sensors and Actuators, 18:309-327 (1989).
Bergveld, P., "ISFET, Theory and Practice," IEEE Sensor Conference, Toronto, Oct. 2003, 26 pages.
Bergveld, P., "Thirty years of ISFETOLOGY What happened in the past 30 years and what may happen in the next 30 years," Sensors and Actuators B, 88:1-20 (2003).
Bhatt, V. D. et al., "Flexible, Low-Cost Sensor Based on Electrolyte Gated Carbon Nanotube Field Effect Transistor for Organo-Phosphate Detection," Sensors, 17:1147 (2017), 11 pages; doi:10.3390/s17051147.
Birrell, S. J. et al., "Sensors for Site-Specific Management," from the Selected Works of Stuart J. Birrell, 1997, pp. 183-210; http://works.bepress.com/stuart_birrell/40/.
Birrell, S. J. & Hummel, J. W., "Multi-sensor ISFET system for soil analysis," Proceedings of the First European Conference on Precision Agriculture, Jan. 1, 1997, 9 pages.
Birrell, S. J., "Membrane Selection and ISFET Configuration Evaluation for Soil Nitrate Sensing," Transactions of the ASAE, 43(2):197-206 (2000); doi: 10.13031/2013.2694.
Birrell, S. J. & Hummel, J. W., "Real-time multi ISFET/FIA soil analysis system with automatic sample extraction," Computers and Electronics in Agriculture, 32:45-67 (2001).
Bolton, D. K. & Friedl, M. A., "Forecasting crop yield using remotely sensed vegetation indices and crop phenology metrics," Agricultural and Forestry Meteorology, 173:74-84 (2013).
Bound, G. P. & Fleet, B., "The Development of a Solid State Reference Electrode for Use in Soil Measurements," J. Sci. Fd Agric, 28:431-435 (1977).
Brau-Avila, A. et al., "Mathematical calibration procedure of a capacitive sensor-based indexed metrology platform," Meas. Sci. Technol., 28:035008 (2017), 12 pages; https://doi.org/10.1088/1361-6501/aa5740.
Bradford, M. A. et al., "A test of the hierarchical model of litter decomposition," Nature Ecology & Evolution, 1:1836-1845 (2017); doi:10.1038/s41559-017-0367-4.
Brouder, S. M. et al., "Potential Uses of Ion-Selective Potassium Electrodes in Soil Fertility Management," Communications in Soil Science and Plant Analysis, 34(19-20): 2699-2726 (2003).
Buck, R. P. & Lindner, E., "Recommendations for Nomenclature of Ion-selective Electrodes," Pure & Appl. Chem., 66(12):2527-2536 (1994).
Bühlmann, P. & Chen, L. D., "Ion-Selective Electrodes With Ionophore-Doped Sensing Membranes," Supramolecular Chemistry: From Molecules to Nanomaterials, First Published: Mar. 15, 2012, 41 pages; doi:10.1002/9780470661345.smc097.
Campbell, E. R. et al., "Determination of phosphate in soil extracts in the field: A green chemistry enzymatic method," MethodsX, 2:211-218 (2015).
Cané, C. et al., "Compatibility of ISFET and CMOS technologies for smarter sensors," Transducers '91: 1991 International Conference on Solid-State Sensors and Actuators. Digest of Technical Papers, Jun. 24-27, 1991, 4 pages.
Cané, C. et al., "Multilayer ISFET membranes for microsystems applications," Sensors and Actuators B, 35-36:136-140 (1996).
Campanella, L. et al., "Sensitive membrane ISFETs for nitrate analysis in waters," Sensors and Actuators B, 26-27:329-335 (1995).
Carey, C. M. & Riggan, W. B., Jr., "Cyclic Polyamine Ionophore for Use in a Dibasic Phosphate-Selective Electrode," Anal. Chem., 66:3587-3591 (1994).
Dumschat, C. et al., "Filled Fluorosilicone as Matrix Material for Ion-selective Membranes," Analyst, 121:527-529 (1996).
Law, A. T. & Adeloju, S. B., "Progress and recent advances in phosphate sensors: A review," Talanta, 114:191-203 (2013).
Matthieu, J. et al., "Multimodal Probe Based on ISFET Electrochemical Microsensor for In-Situ Monitoring of Soil Nutrients in Agriculture," Proceedings, 1, 420 (2017), 4 pages; doi:10.3390/proceedings1040420.
Matthieu, J. et al., "All-solid-state multimodal probe based on ISFET electrochemical microsensors for in-situ soil nutrients monitoring in agriculture," 2017 19th International Conference on Solid-State Sensors, Actuators and Microsystems, Transducers 2017, Kaohsiung, Taiwan, Jun. 18-22, 2017, IEEE, pp. 222-225 (2017).
Pursals, J. T., "Desenvolupament de sensors potenciomètrics d'estat sólid per a usos mediambientals i agroalimentaris," Universitat de Barcelona, Doctoral Dissertation, May 2003, with machine English Translation, "Development of enzymatic and immunological biosensor systems based on a renewable mangetic support," 164 pages; Part 1.
Pursals, J. T., "Desenvolupament de sensors potenciometrics d'estat solid per a usos mediambientals i agroalimentaris," Universitat de Barcelona, Doctoral Dissertation, May 2003, with machine English Translation, "Development of enzymatic and immunological biosensor systems based on a renewable mangetic support," 185 pages; Part 2.
Pursals, J. T., "Desenvolupament de sensors potenciometrics d'estat solid per a usos mediambientals i agroalimentaris," Universitat de Barcelona, Doctoral Dissertation, May 2003, with machine English Translation, "Development of enzymatic and immunological biosensor systems based on a renewable mangetic support," 118 pages; Part 3.
Ridder, S., "Innovative solutions with LoRaWAM," 10th LoRa Alliance Open House Chairwoman's Welcome, Jun. 7, 2015, pp. 35-43, 9 pages; https://lora-alliance.org/sites/default/files/2018-06/LoRa%20Alliance%200H%20Master%20Slide%20Deck%20%28June%207%2C%202018%29.pdf.
Sasaki, S. et al., "Organic tin compounds combined with anionic additives-an ionophore system leading to a phosphate ion-selective electrode?" Talanta, 63:131-134 (2004).
Sibbald, A. et al., "A miniature flow-through cell with a four-function chemfet integrated circuit for simultaneous measurements of potassium, hydrogen, calcium and sodium ions," analytica Chimica Acta, 159:47-62 (1984).
Teralytic Web Pages PowerPoint Presentation, Aug. 6, 2018, 10 pages; https://worldagritechusa.com/wp-content/uploads/2018/03/Steven-Ridder-Teralytic.pdf.
Van Den Berg, A. & Grisel, A., "A universal on-wafer fabrication technique for diffusion limiting membranes for use in microelectrochemical amperometric sensors," Sensors and Actuators B, 5:71-74 (1991).
Van Den Berg et al., "Miniaturized Chemical Analysis Systems," 1994 5th International Symposium on Micro Machine and Human Science Proceedings, Oct. 2-4, 1994, IEEE, pp. 181-184; doi:10.1109/ISMMHS.1994.512921.

* cited by examiner

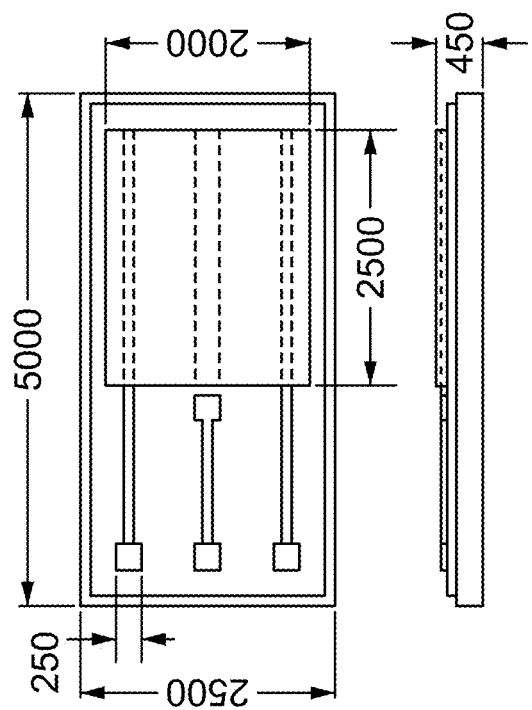
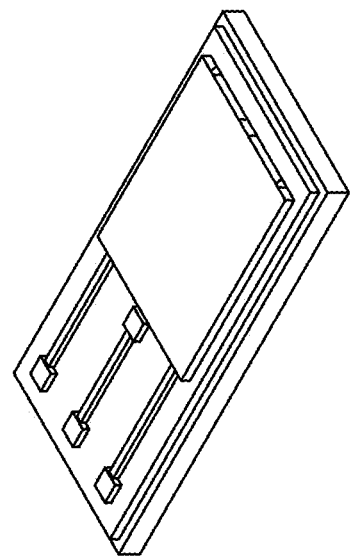
FIG. 7A
FIG. 7B

EXTENSIBLE, MULTIMODAL SENSOR FUSION PLATFORM FOR REMOTE, PROXIMAL TERRAIN SENSING

CROSS-REFERENCE TO RELATED APPLICATIONS

This application claims priority to and the benefit of U.S. Provisional Patent Application No. 62/734,639, titled "ISFET and CHEMFET Based Sub-Soil Sensor Assemblies," filed Sep. 21, 2018, the disclosure of which is hereby incorporated by reference in its entirety.

BACKGROUND

Sensors, such as moisture sensors, are used by farmers and gardeners to measure soil properties.

SUMMARY

A sensor assembly includes a housing with one or more sensor array segments. One sensor array segment includes wireless communication hardware, such as an antenna, and optionally, also includes an air temperature sensor, a humidity sensor, and a light sensor. Another sensor array segment includes a soil temperature sensor, an electrical conductivity (EC) sensor, a moisture sensor, and a sub-array. The sub-array includes multiple ion-sensitive field-effect transistor (ISFET) sensors including at least one ISFET sensor for pH measurement. At least one ISFET sensor of the sub-array includes a single-layer ruggedized membrane or a multi-layer ruggedized membrane for the selective detection of at least one of: ammonium, calcium, carbonate, chloride, nitrate, phosphate, potassium, sodium, or sulfate, in adjacent soil. A solid-state reference electrode is either electrically coupled to each ISFET sensor or shared via multiplexing circuit. Optionally, an additional sensor sub-array contains ion-selective electrodes, also electrically coupled to the reference electrode and shared via multiplexing circuit. The first sensor array segment and the reference electrode can be disposed on opposite sides of the second sensor array segment.

BRIEF DESCRIPTION OF THE DRAWINGS

FIGS. 7A-7B are schematic drawings of a sensor die, according to an embodiment.

DETAILED DESCRIPTION

Figure 1A:
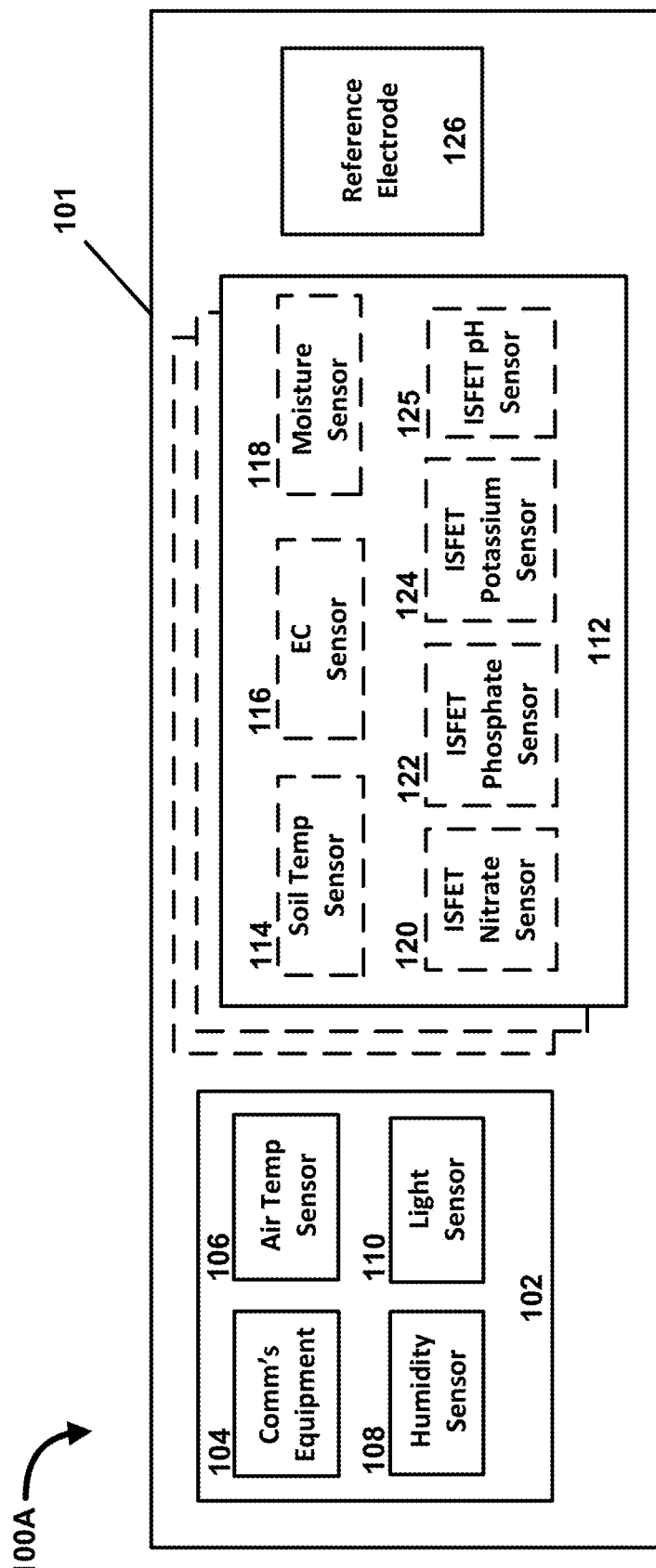
FIGS. 1A-1C are block diagrams showing sensor assembly configurations, according to some embodiments.

Existing soil sensing architectures typically rely on dedicated sensors that are designed to detect individual soil properties, such as moisture. As such, measuring multiple soil properties can become cumbersome, due to the need to include multiple discrete sensors, with their associated overhead (e.g., cabling, electronics, etc.). Moreover, known sensors are often fabricated from materials that rapidly degrade in the presence of soil, and therefore can exhibit a relatively short lifetime and a lack of predictability and stability in their performance.

Embodiments of the present disclosure address the above drawbacks of existing soil sensor technologies. For example, sensor assemblies of the present disclosure include one or multiple sensor blocks, each sensor block including sensors (e.g., arranged in rows or arrays) for detecting a wide range of soil conditions and nutrients. Sensors of the present disclosure include ruggedized, ion-sensitive membranes and are configured to withstand soil environments for substantially longer than known sensors. In some embodiments, one or more sensors of a sensor assembly is PVC-free. Alternatively or in addition, in some embodiments, a sensor assembly includes a copper-free reference electrode.

A sensor assembly (also referred to herein as a "stake" or "probe") of the present disclosure can include multiple sensors (i.e., a "suite" of sensors), including, but not limited to, sensors for temperature, humidity, light, soil moisture, electrical conductivity, pH, and one or more soil nutrients. The nutrients that can be sensed by sensor embodiments of the present disclosure include, but are not limited to, ammonium ($NH_4^+$), calcium ($Ca^{2+}$), carbon dioxide/carbonates ($CO_2$, $HCO_3^-$, and $CO_3^{2-}$, depending on pH), chloride ($Cl^-$), nitrate ($NO_3^-$), phosphates ($H_3PO_4$, $H_2PO_4^-$, $HPO_4^{2-}$, and $PO_4^{3-}$, depending on pH), potassium ($K^+$), sodium ($Na^+$), and sulfate ($SO_4^{2-}$).

A wide range of nutrients can be detected using ion-sensitive field-effect transistor (ISFET) and/or chemically-sensitive field-effect transistor (ChemFET) sensors. The ISFETs described herein facilitate an extensible, versatile platform for the detection of a wide variety of soil nutrients. An ISFET, in its base configuration, can sense protons ($H^+$), thereby enabling pH monitoring. Through the deposition of a membrane on the exposed gate of an ISFET, the ISFET can be transformed into a ChemFET with chemical sensitivity. The sensor assembly can be configured to perform real-time or quasi-real-time transmission of key soil health metrics to the end user, as part of a precision agriculture system. Historically, ISFETs or ChemFETs have not been considered suitable for use in soil sensing contexts, for example due to durability issues, as discussed above. In the present disclosure, however, several methods are presented for improving the durability and stability of sensors, rendering them suitable for agricultural use. Key improvements include improved membrane materials and solid-state reference electrodes designed for long lifetimes in soil.

Sensor Assemblies

In some embodiments, the form factor of a sensor assembly (or "platform") is that of an elongate "stake" (e.g., suitable for insertion into the ground), with multiple sensors positioned therein and/or thereon at defined levels, for detecting and reporting nutrient levels (and/or other conditions) at corresponding levels/depths in soil. The multiple sensors can include (but are not limited to): ammonium ISFET sensor(s), calcium ISFET sensor(s), carbonate ISFET sensor(s), chloride ISFET sensor(s), nitrate ISFET sensor(s), phosphate ISFET or electrode sensor(s), potassium ISFET sensor(s), sodium ISFET sensor(s), sulfate ISFET sensor(s) and pH ISFET sensors, electrical conductivity (EC) sensor(s), soil moisture sensor(s), and temperature sensor(s). In some embodiments, the platform can include 1, 2, 3, 4, 5, 6, 7, 8, 9, 10, 11, 12, 13, 14, 15, 16, 17, 18, 19, 20, or more ISFET sensors, inclusive of all ranges and values therebetween. The sensor assembly can include one or more "sensor blocks," each sensor block including one or more sensors, each sensor block (or an active/exposed region thereof) being positioned at a predetermined location in or on a housing of the sensor assembly (e.g., centered at or beginning at about 6" (15 cm), about 12" (30 cm), about 18" (45 cm), and/or about 36" (90 cm) below the ground level). Depending on the implementation, some or all sensors in the sensor assembly are configured to be at least partially in direct contact with the soil once installed. In view of their direct contact with a soil environment during use, sensors (e.g., including sensor membranes) and sensor assemblies (e.g., including sensor assembly housings) of the present disclosure are designed to be durable, and resistant to a wide variety of soil environments.

In some embodiments, the sensor assembly includes a suite of sensors in a sensor probe head (or "probe head"), which includes wireless communications hardware and/or wired communications hardware. Each probe head can also include sensors for one or more of: air temperature, humidity, and light. In some such implementations, one or more carbon dioxide ($CO_2$) gas sensors can be located at specific locations on or in the sensor assembly, for example at approximately 6" (15 cm) below a surface of the soil. Alternatively, or in addition, in some such implementations, oxygen gas ($O_2$) sensors can be located at specific locations on or in the sensor probe, for example at approximately 18" (45 cm) below a surface of the soil. Alternatively or in addition, ammonia ($NH_3$), nitrous oxide ($N_2O$), or methane ($CH_4$) gas sensors can be located at specific locations throughout the probe. A single, common solid-state reference electrode can be located at the tip of the sensor stake, or individual reference electrodes may be located near each sensor array. The reference electrodes can be shared electrically, for example via multiplexing circuits.

Figure 1B:
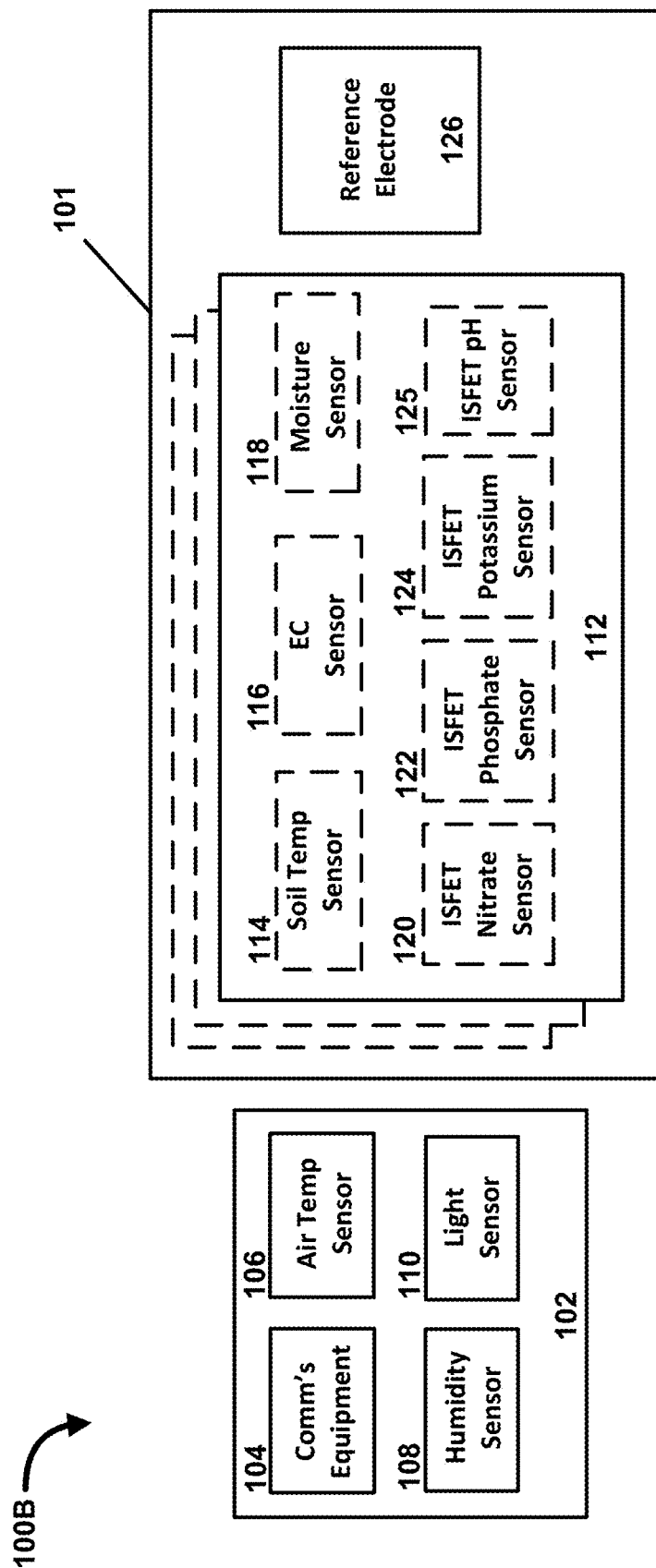
Figure 1C:
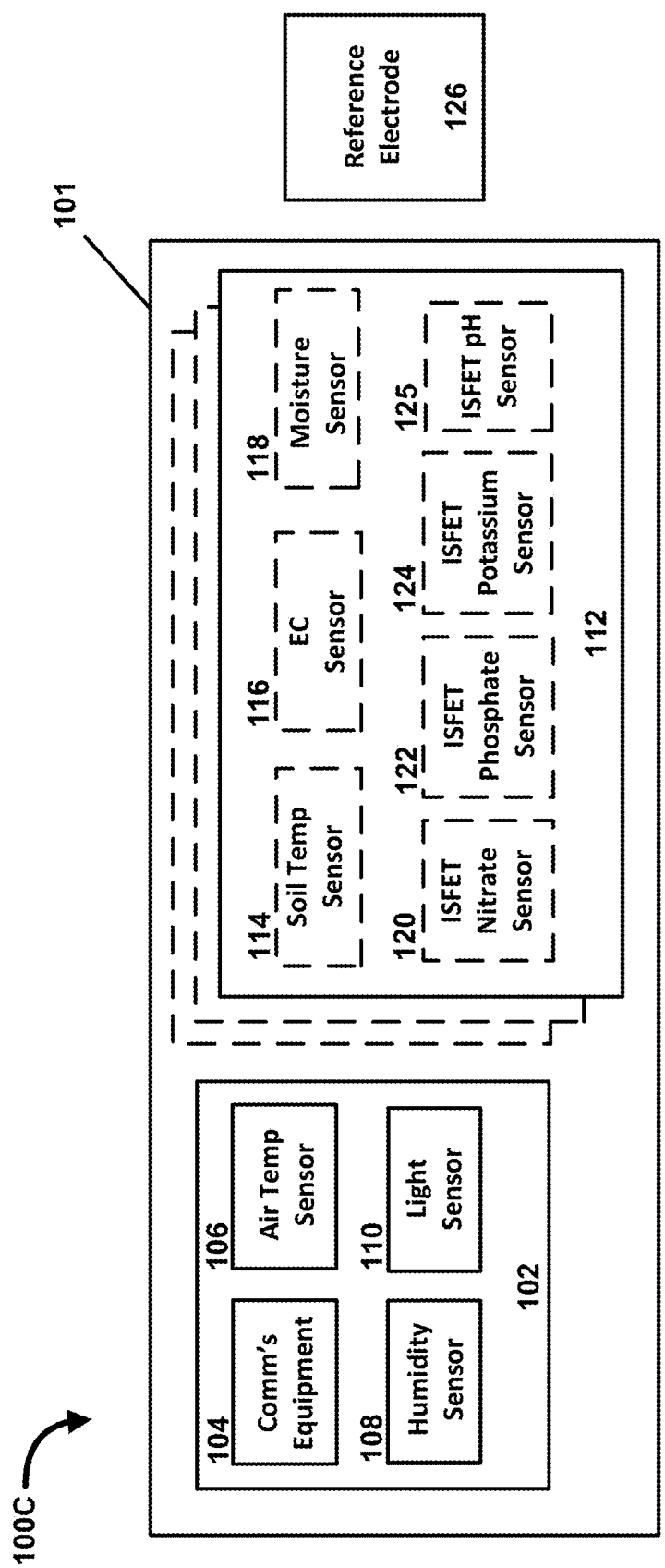

FIGS. 1A-1C are block diagrams showing sensor assembly configurations, according to some embodiments. As shown in FIG. 1A, a sensor assembly 100A includes a housing 101, a first sensor array segment 102 ("probe head"), one or more second sensor array segments 112 ("sensor block(s)"), and a reference electrode 126. The housing 101 can have any of a variety of different geometries and/or shapes, including but not limited to: elongate, disc-shaped, circular, sheet-like, and/or plate-like. The first sensor array segment 102 is disposed within the housing 101, and includes communications-related equipment 104 (e.g., antenna, transceiver, wired communication components, processor and associated memory, etc.), and optionally one or more of an air temperature sensor 106, a humidity sensor 108, and a light sensor 110. The one or more second sensor array segments 112 are disposed within the housing 101, and include one or more of: a soil temperature sensor 114, an electrical conductivity (EC) sensor 116, a moisture sensor 118, an ion-sensitive field effect transistor (ISFET) nitrate sensor 120, an ISFET phosphate sensor 122, an ISFET potassium sensor 124, and an ISFET pH sensor 125. The nitrate sensor 120 is configured to detect, during use and substantially in real time, nitrates in an adjacent region of soil. The phosphate sensor 122 is configured to detect, during use and substantially in real time, phosphates in an adjacent region of soil. The potassium sensor 124 is configured to detect, during use and substantially in real time, potassium in an adjacent region of soil. The pH sensor 125 is configured to detect, during use and substantially in real time, pH in an adjacent region of soil. The reference electrode 126 is electrically coupled to each of the first sensor array segment 102 and the second sensor array segment(s) 112. The first sensor array segment 102 is disposed on a first (left) side of the second sensor array segment(s) 112, and the reference electrode 126 is disposed on a second side of the second sensor array segment(s) 112, the second side of the second sensor array segment(s) 112 opposite the first side of the second sensor array segment(s) 112. In some embodiments, one or more of the sensor array segment 102, the one or more second sensor array segments 112, or the reference electrode 126 is removably coupled to or disposed within the sensor assembly 100A, such that it can be replaced. The removable coupling can be accomplished via any suitable means, such as screw-thread engagement, mechanical attachment (e.g., snaps, clamps, etc.), adhesive attachment, press-fit attachment, etc.

FIG. 1B includes elements similar to those of FIG. 1A, but with the first sensor array segment 102 disposed outside (and configured to be attached to) the housing 101. FIG. 1C includes elements similar to those of FIG. 1A, but with the reference electrode 126 disposed outside (and configured to be attached to) the housing 101.

Sensors of the sensor assemblies (e.g., 100A, 100B, 100C) can be calibrated prior to use, as discussed further below with reference to FIGS. 20-23, and the associated calibration curves can be analyzed and/or stored in firmware or remotely. The firmware can reside in one or more of: the first sensor array segment (e.g., first sensor array segment 102), the one or more second sensor array segments (e.g., one or more second sensor array segments 112), or "the cloud" (i.e., a cloud computing network).

Figures 2A, 2B:
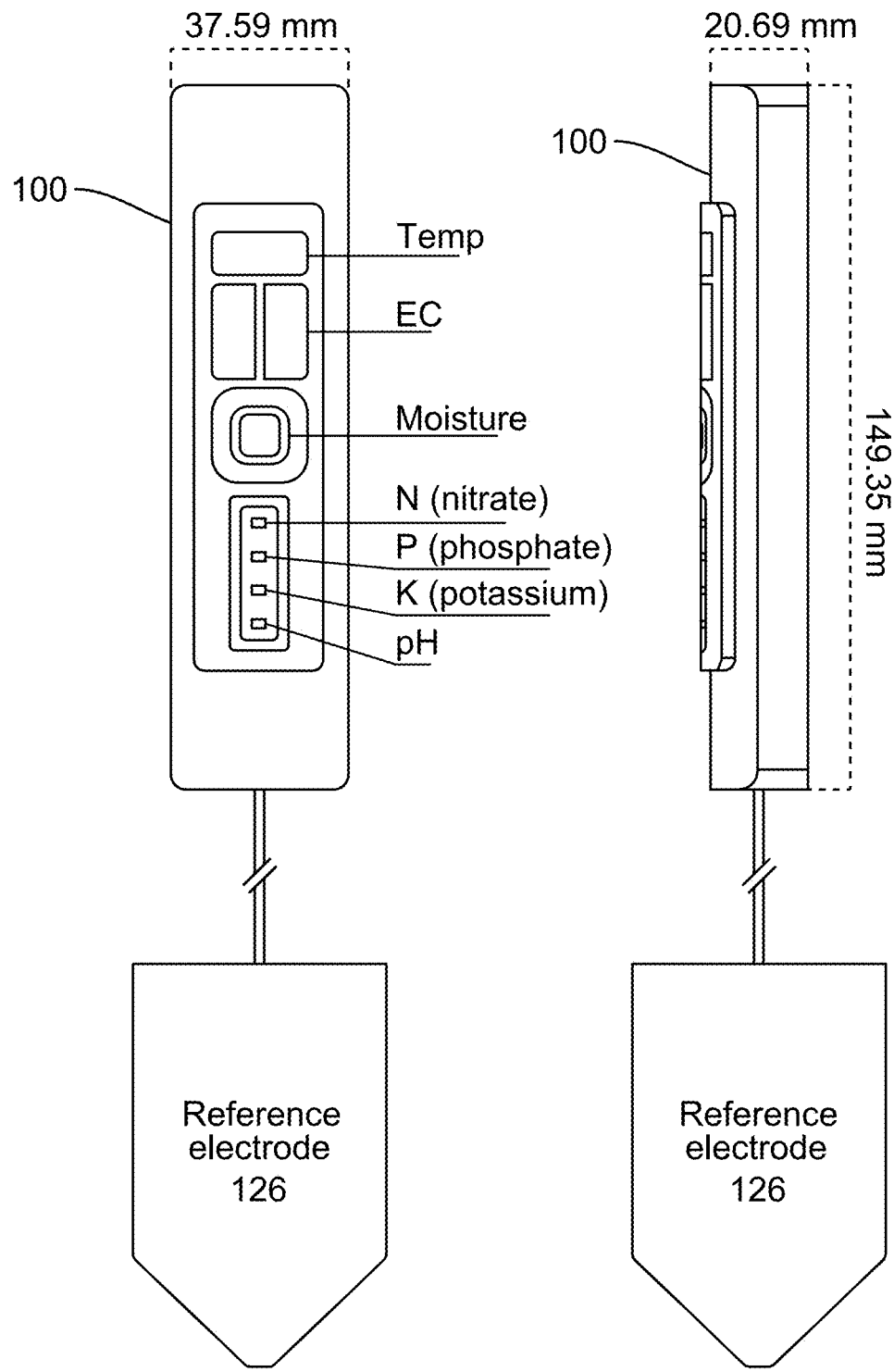
FIGS. 2A-2B are drawings of a sensor assembly (front and side views, respectively), according to an embodiment.
Figure 3:
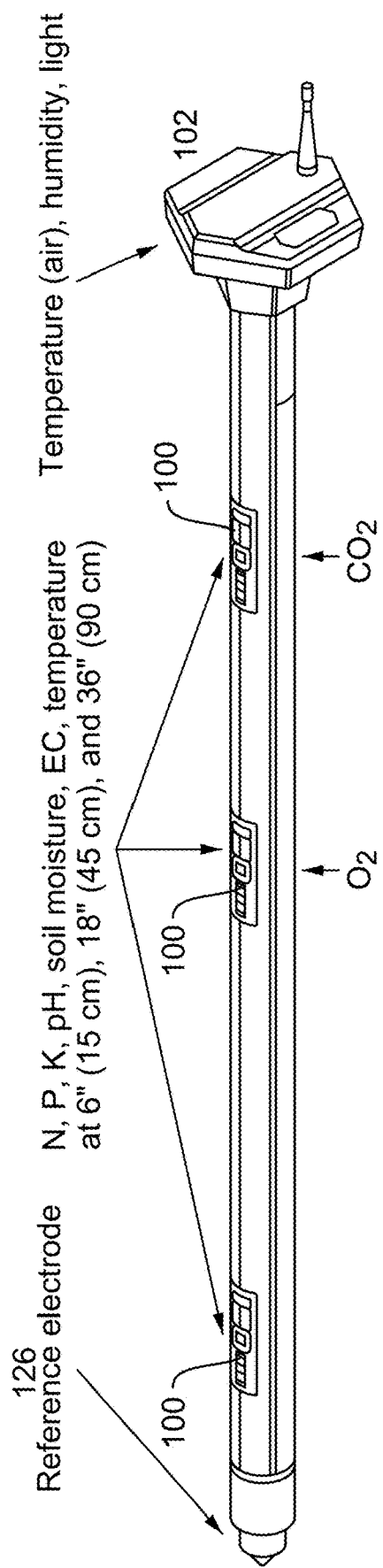
FIG. 3 is a drawing of a sensor assembly including three sensor blocks, according to an embodiment.

Diagrams depicting an individual sensor block 100 (e.g., similar to sensor blocks 112 of FIGS. 1A-1C) coupled to a large reference electrode 126 are shown in FIGS. 2A-2B. As shown in FIGS. 2A-2B, a sensor block 100 can include a 4-sensor ISFET array with nitrate, phosphate, potassium, and pH ISFET sensors, along with electrical conductivity (EC), soil moisture, and temperature sensors, at each of a plurality of positions in/on each sensor block of the sensor assembly. An example of a sensor assembly having three sensor blocks (such as the sensor block shown in FIGS. 2A-2B), each coupled to a single common, large reference electrode 126, is shown in FIG. 3.

Figures 4A, 4B:
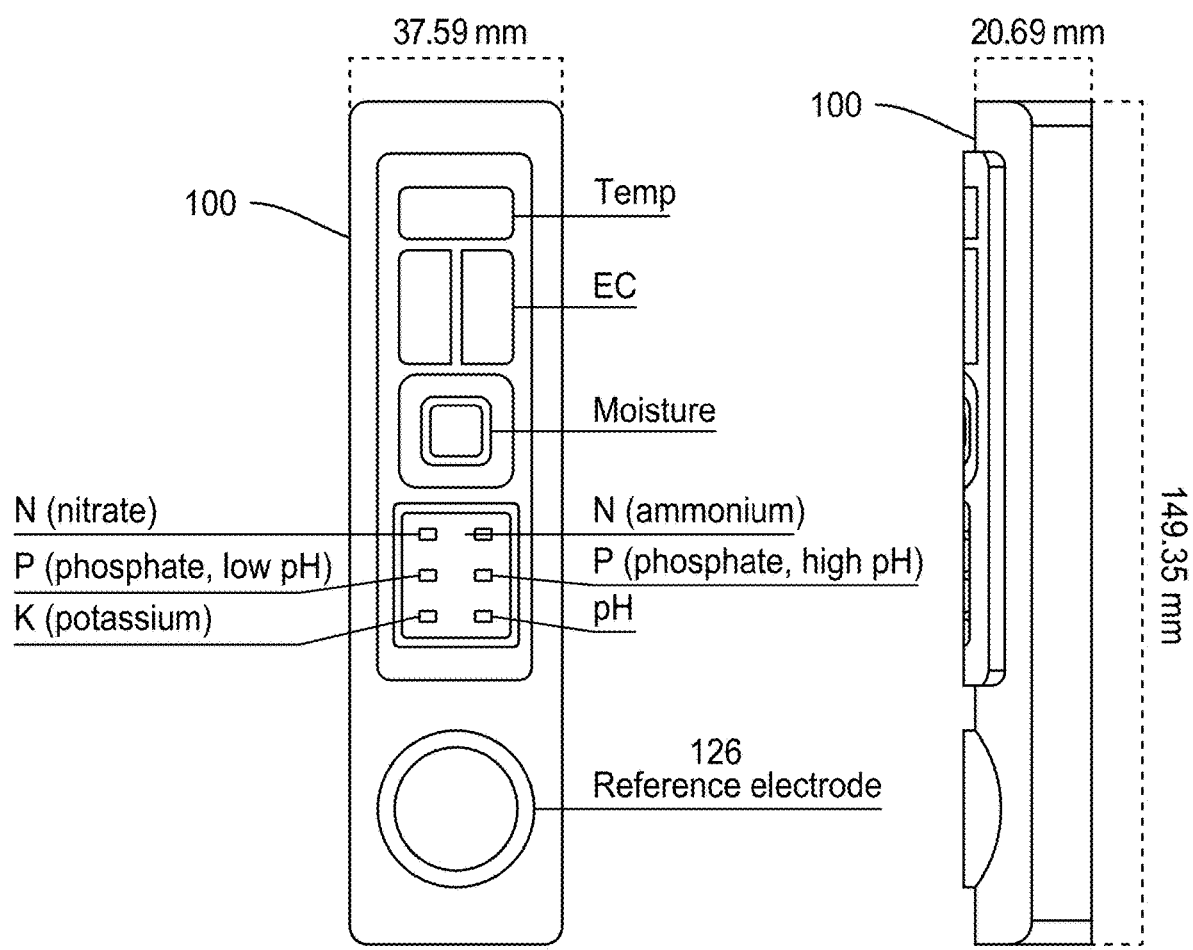
FIGS. 4A-4B are drawings of a sensor assembly (front and side views, respectively), according to an embodiment.
Figure 5:
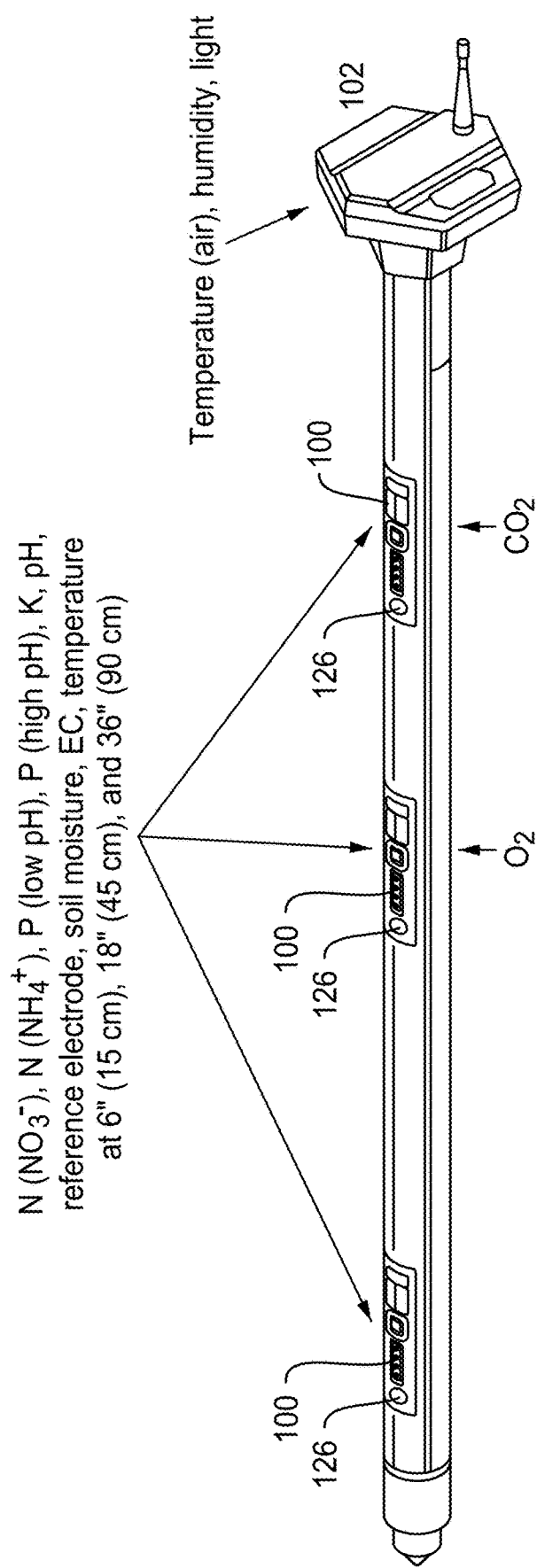
FIG. 5 is a drawing of a sensor assembly including three sensor blocks, according to an embodiment.
Figure 6B:
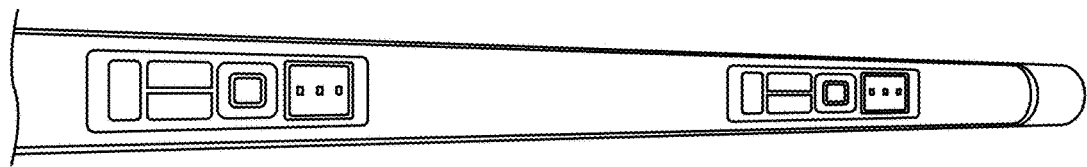
FIGS. 6A-6D are photographs of a sensor assembly including three sensor blocks, according to an embodiment.
Figure 6A:
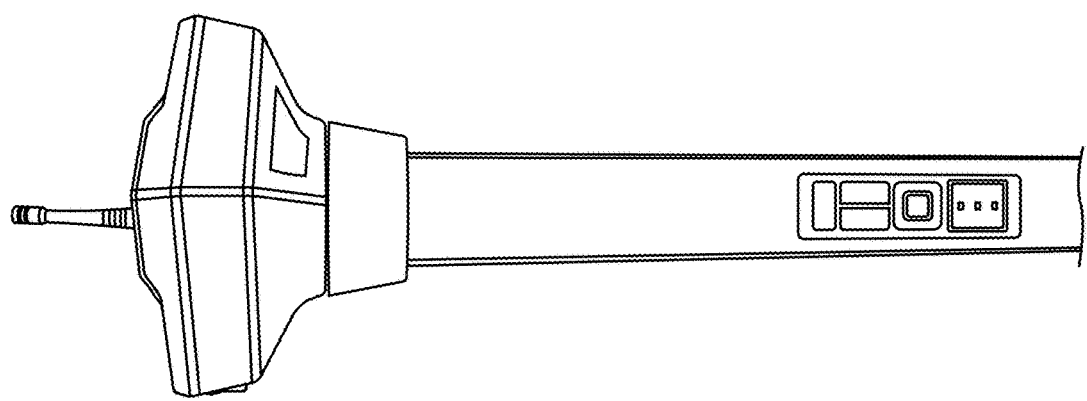
Figure 6D:
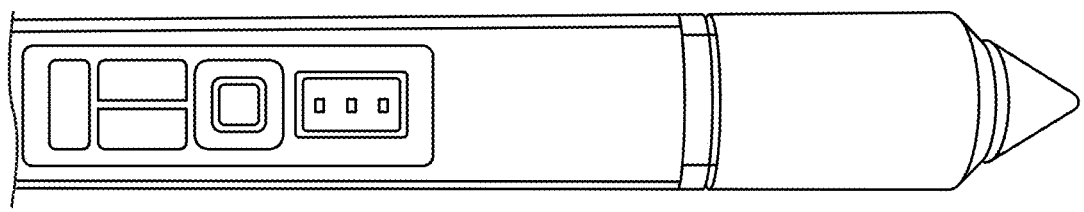
Figure 6C:
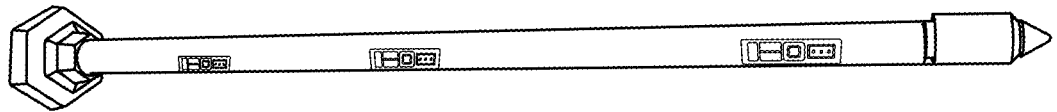

Diagrams depicting an individual sensor block 100 (e.g., similar to sensor blocks 112 of FIGS. 1A-1C) including a mini reference electrode 126 are shown in FIGS. 4A-4B. As shown in FIGS. 4A-4B, a sensor block 100 includes a 6-sensor ISFET array with nitrate, ammonium, low-pH phosphate, high-pH phosphate, potassium, and pH ISFET sensors, along with EC, soil moisture, and temperature sensors, at each of a plurality of positions in/on each sensor block of the sensor assembly, where each position corresponds to a soil depth during use. Substitutions may be made, where one nutrient sensor is replaced with another, e.g. a sulfate or calcium ISFET sensor may replace the phosphate ISFET sensor(s). In some such configurations, small, or "mini," reference electrodes are disposed adjacent to (rather than incorporated within) each sensor block, and connected to an associated set of individual ISFET circuits of the sensor block. An example of a sensor assembly having three sensor blocks (such as the sensor block shown in FIGS. 4A-4B), each coupled to an associated mini reference electrode 126 (rather than to a common large reference electrode), is shown in FIG. 5.

FIGS. 6A-6D are photographs of a constructed sensor assembly including three sensor blocks, according to an embodiment.

Sensor Dies

Figure 8A:
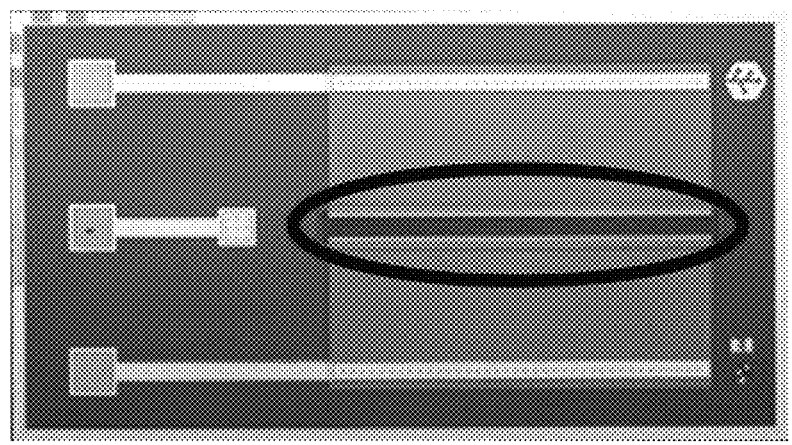
FIG. 8A is a photograph of a sensor die, according to an embodiment.

FIGS. 7A-7B are schematic drawings of an example sensor die, according to an embodiment. As shown in FIG. 7A, a sensor die can have a rectangular shape with a length of about 2,500 micrometers ($\mu m$) and a width of about 5,000 $\mu m$. Bond pads of the conductive traces (connected to one or more ISFETs of the sensor die) can be about 250 $\mu m$ by about 250 $\mu m$ square. An active region of the sensor die can have a rectangular shape with a size of about 2,000 $\mu m$ by about 2,500 $\mu m$. Sensor dies can be fabricated on rigid substrates, such as silicon wafers, or on flexible substrates, such as polyethylene terephthalate (PET). Although example geometries for the sensor die are presented in FIG. 7A, deviations from the sizes and/or proportionalities of the various sensor die features can be made without departing from the scope of the present disclosure. In some embodiments, the sensor die can have a length of about 500 $\mu m$, about 1,000 $\mu m$, about 1,500 $\mu m$, about 2,000 $\mu m$, about 2,500 $\mu m$, about 3,000 $\mu m$, about 3,500 $\mu m$, about 4,000 $\mu m$, about 4,500 $\mu m$, or about 5,000 $\mu m$, inclusive of all ranges therebetween. In some embodiments, the sensor die can have a width of about 500 $\mu m$, about 1,000 $\mu m$, about 1,500 $\mu m$, about 2,000 $\mu m$, about 2,500 $\mu m$, about 3,000 $\mu m$, about 3,500 $\mu m$, about 4,000 $\mu m$, about 4,500 $\mu m$, or about 5,000 $\mu m$, inclusive of all ranges therebetween. In some embodiments, the sensor die can have a thickness of about 100 $\mu m$, about 150 $\mu m$, about 200 $\mu m$, about 250 $\mu m$, about 300 $\mu m$, about 350 $\mu m$, about 400 $\mu m$, about 450 $\mu m$, about 500 $\mu m$, about 550 $\mu m$, about 600 $\mu m$, about 650 $\mu m$, about 700 $\mu m$, about 750 $\mu m$, about 800 $\mu m$, about 850 $\mu m$, about 900 $\mu m$, about 950 $\mu m$, about 1,000 $\mu m$ (1 mm), about 1,050 $\mu m$, about 1,100 $\mu m$, about 1,150 $\mu m$, about 1,200 $\mu m$, about 1,250 $\mu m$, about 1,300 $\mu m$, about 1,350 $\mu m$, about 1,400 $\mu m$, about 1,450 $\mu m$, about 1,500 $\mu m$, about 1,550 $\mu m$, about 1,600 $\mu m$, about 1,650 $\mu m$, about 1,700 $\mu m$, about 1,750 $\mu m$, about 1,800 $\mu m$, about 1,850 $\mu m$, about 1,900 $\mu m$, about 2,000 $\mu m$ (2 mm), inclusive of all ranges therebetween As described above, nutrient sensing, according to some embodiments, can be achieved via sensor dies using ISFETs or ChemFETs, which are amenable to fabrication via high-volume CMOS processing. A representative geometry of an ISFET sensor die is shown in the light microscope photograph of FIG. 8A. These devices evince common transistor-like structures, however, the metal gate normally associated with a transistor has been removed and left exposed. In some embodiments, it is the exposed region (see circled region in FIG. 8A) that is disposed adjacent to soil during use, and is responsible for ion or nutrient sensing (e.g., via one or multiple ion-sensitive membranes). The exposed region prior to membrane deposition can include one or more materials such as such as carbon, graphene, carbon nanotubes, or films including silicon nitride ($Si_3N_4$), aluminum oxide ($Al_2O_3$), or tantalum oxide ($Ta_2O_5$). The exposed region can be smaller than or larger than the active region discussed above with reference to FIG. 7A.

There is a design trade-off between allowing a portion of the sensor to contact the soil or medium of interest, while also protecting sensitive electronics. In some embodiments, the electronics are "encapsulated" using a material such as epoxy or resin. A portion of the active region of the sensor can be left exposed after the encapsulation process is completed. This can be accomplished, for example, by "masking" (or otherwise protecting) the desired region to be exposed, such that no encapsulant material is applied thereto during the encapsulation process (e.g., during an "additive" encapsulation process, in which encapsulant material is added to the surface of the die/PCB). Alternatively, or in addition, the active region of the sensor die is first coated with the encapsulant material, and then a portion of the active region (corresponding to the desired region to be exposed) is exposed through a subtractive process (e.g., dry etching, wet chemical etching, mechanical removal, etc.).

Figure 8B:
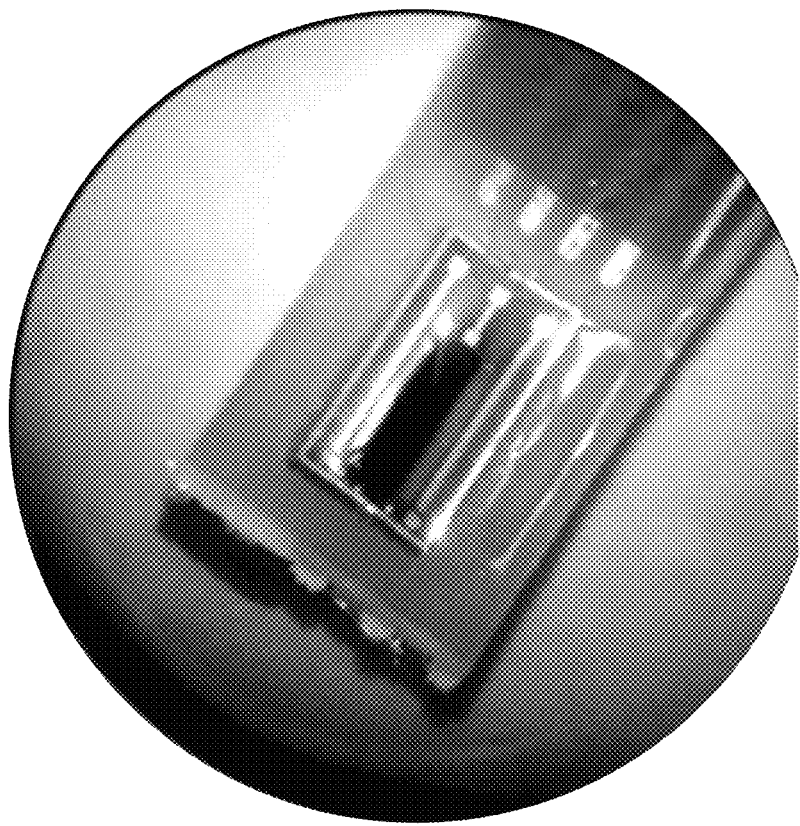
FIG. 8B is a photograph of a sensor die mounted on a circuit board and encapsulated, according to an embodiment.

An example of an encapsulated ChemFET sensor die mounted on a printed circuit board (PCB) is shown in the photograph of FIG. 8B. Additional examples of encapsulation can be seen in FIG. 15 with a 4-sensor ISFET/Chem- FET array and FIG. 16 with a set of boards containing 6-sensor ISFET/ChemFET arrays.

Ion-Sensitive Membrane Synthesis and Deposition

Matrix Materials and Processing

In some embodiments, membranes (formed from a "matrix material") are synthesized and disposed on an exposed gate of a field-effect transistor (FET) for the detection of analytes. The analytes that can be detected by a membraned FET include, but are not limited to, ammonium, calcium, carbonate, chloride, nitrate, phosphate, potassium, sodium, and sulfate. A matrix material, as defined herein, can include a fluorosilicone (FS) sealant/adhesive, or other polymeric materials having mechanical properties that achieve satisfactory ratings under ASTM standards, such as ASTM D3359 (Standard Test Methods for Rating Adhesion by Tape Test) and ASTM D6677 (Evaluating Adhesion by Knife). For example, membranes can receive a rating of 5A (no peeling or removal) under ASTM D3359 Test Method A and a rating of 7 or higher under ASTM D6677.

In some embodiments, various additives may be added to the matrix materials to tailor electrical properties, for example, the addition of carbon black. Prior to the inclusion of ion-selective ionophores and other ionic additives, the FS matrix material can be dissolved in a suitable solvent, such as tetrahydrofuran (THF) or cyclohexanone. Alternatively, matrix materials can include one or more ionophore-doped conducting polymers (CPs), such as polyaniline (PANI), polypyrrole (PPy), poly(3,4-ethylenedioxythiophene) (PEDOT), or poly(3-octylthiophene) (POT), as examples. Alternatively or in addition, a sensor array can include FS, CPs, or a mixture thereof.

In some embodiments, membrane solutions including FS or CPs are dispensed on the exposed gate of the field-effect transistor to yield an ion-selective membrane. The dispensing of the matrix material onto the exposed gate can include one or more of: screen printing, inkjet printing, syringe dispensing, etc. The membrane material(s) may be allowed to cure in air or other ambient environments, or via vacuum processing. Photocurable membranes may be cured via UV/visible light exposure.

Ammonium-Sensing Membranes

In some embodiments, to achieve ion selectivity for ammonium ($NH_4^+$), the ionophore nonactin, monactin, or a mixture thereof is added to the dissolved matrix material. Optionally, the ionic additive potassium tetrakis(4-chlorophenyl)borate can also be added. The matrix material, in some embodiments, may be present in amounts ranging from about 30% to about 90% (w/w), with the balance comprising ionophores, ionic additives, and plasticizers in varying ratios.

Calcium-Sensing Membranes

In some embodiments, to achieve ion selectivity for calcium ($Ca^{2+}$), the ionophore diethyl N,N'-[(4R,5R)-4,5-dimethyl-1,8-dioxo-3,6-dioxaoctamethylene]bis(12-methylamino-dodecanoate) (ETH 1001), N,N,N',N'-tetracyclohexyl-3-oxapentanediamide (ETH 129), calcimycin, N,N-dicyclohexyl-N',N'-dioctadecyl-3-oxapentanediamide (ETH 5234), 10,19-bis[(octadecylcarbamoyl)methoxyacetyl]-1,4,7,13,16-pentaoxa-10,19-diazacycloheneicosane, α-furildioxime, or a mixture thereof is added to the dissolved matrix material. Optionally, the ionic additive sodium tetrakis[3,5-bis(trifluoromethyl)phenyl]borate (NaTFPB) can also be added. The matrix material, in some embodiments, may be present in amounts ranging from 30%-90% (w/w) or thereabouts, with the balance comprising ionophores, ionic additives, and plasticizers in varying ratios.

Carbonate-Sensing Membranes

In some embodiments, to achieve ion selectivity for carbonate ($CO_3^{2-}$), the ionophore heptyl 4-trifluoroacetylbenzoate (ETH 6010), 1-(dodecyl sulfonyl)-4-trifluoroacetylbenzene (ETH 6019), N-dodecyl-N-(4-trifluoroacetylphenyl)acetamide (ETH 6022), 4-butyl-α,α,α-trifluoroacetophenone, N,N-dioctyl-3α,12α-bis(4-trifluoroacetylbenzoyloxy)-5β-cholan-24-amide, or a mixture thereof is added to the dissolved matrix material. Optionally, the ionic additive tridodecylmethylammonium chloride (TDMAC) can also be added. The matrix material, in some embodiments, may be present in amounts ranging from 30%-90% (w/w) or thereabouts, with the balance comprising ionophores, ionic additives, and plasticizers in varying ratios.

Chloride-Sensing Membranes

In some embodiments, to achieve ion selectivity for chloride ($Cl^-$), the ionophore meso-tetraphenylporphyrin manganese(III)-chloride complex, 4,5-dimethyl-3,6-dioctyloxy-o-phenylene-bis(mercurytrifluoroacetate) (ETH 9009), 3,6-didodecyloxy-4,5-dimethyl-o-phenylene-bis(mercury chloride) (ETH 9033), 4,5-bis-[N'-(butyl)thioureido]-2,7-di-tert-butyl-9,9-dimethylxanthene, or a mixture thereof is added to the dissolved matrix material. Optionally, the ionic additive tridodecylmethylammonium chloride (TDMAC) can also be added. The matrix material, in some embodiments, may be present in amounts ranging from 30%-90% (w/w) or thereabouts, with the balance comprising ionophores, ionic additives, and plasticizers in varying ratios.

Nitrate-Sensing Membranes

In some embodiments, to achieve ion selectivity for nitrate ($NO_3^-$), the ionophore α,α,α,α-5,10,15,20-tetrakis{2-[3-(4-methylphenyl)ureido]phenyl}porphyrine, 1,6,10,15-tetraoxa-2,5,11,14-tetraazacyclooctodecane, [1,3,8,10] tetraazacyclotetradecine-10,21-dithione, 9-hexadecyl-1,7,11,17-tetraoxa-2,6,12,16-tetraazacycloeicosane, or a mixture thereof is added to the dissolved matrix material. Optionally, tridodecylmethylammonium nitrate, tetradodecylammonium nitrate, tri-n-octylmethylammonium nitrate, or other quarternary ammoniun salts may can also be added. The matrix material, in some embodiments, may be present in amounts ranging from 30%-90% (w/w) or thereabouts, with the balance comprising ionophores, ionic additives, and plasticizers in varying ratios.

Phosphate-Sensing Membranes

In some embodiments, to achieve ion selectivity for the phosphates in the pH regime of approximately 2-7, tin organometallics, such as tributyltin chloride (TBTC), are added to the dissolved matrix material. Ionic additives such as sodium tetrakis [3,5-bis(trifluoromethyl)-phenyl]borate (NaTFPB) may be added in varying mol % relative to the tin organometallics. To achieve ion selectivity for the phosphates in the pH regime of approximately 7-12, cyclic polyamines such as the $N_3$-, $N_4$-, $N_5$-, and $N_6$-cyclic amines are used as ionophores. NaTFPB may be added in varying mol % relative to the cyclic amines. The matrix material, in some embodiments, may be present in amounts ranging from 30%-90% (w/w) or thereabouts, with the balance comprising ionophores, ionic additives, and plasticizers in varying ratios. In some embodiments, multiple ISFET-based phosphate sensors are coupled to cover a wider pH range, and these sensors may also be correlated to electrode-based sensors, such as those fabricated from cobalt wires, enabling the sensor to detect a broad spectrum of phosphate species in soil.

Potassium-Sensing Membranes

In some embodiments, to achieve ion selectivity for potassium, the ionophore valinomycin is added to the dissolved matrix material. Optionally, the ionic additives potassium tetrakis(4-chlorophenyl)borate (KT4ClPB) and/or sodium tetrakis [3,5-bis(trifluoromethyl)phenyl]borate (NaTFPB) can also be added. The matrix material, in some embodiments, may be present in amounts ranging from 30%-90% (w/w) or thereabouts, with the balance comprising ionophores, ionic additives, and plasticizers in varying ratios.

Sodium-Sensing Membranes

In some embodiments, to achieve ion selectivity for sodium ($Na^+$), the ionophore N,N',N"-triheptyl-N,N',N"-trimethyl-4,4',4"-propylidynetris(3-oxabutyramide) (ETH 227), N,N'-dibenzyl-N,N'-diphenyl-1,2-phenylenedioxydiacetamide (ETH 157), N,N,N',N'-tetracyclohexyl-1,2-phenylenedioxydiacetamide (ETH 2120), 2,3:11,12-didecalino-16-crown-5, bis[(12-crown-4)methyl]dodecylmethylmalonate, bis[(12-crown-4)methyl] 2,2-didodecylmalonate, 4-tert-butylcalix[4]arene-tetraacetic acid tetraethyl ester, or a mixture thereof is added to the dissolved matrix material. Optionally, the ionic additive sodium tetrakis[3,5-bis(trifluoromethyl)phenyl]borate (NaTFPB) can also be added. The matrix material, in some embodiments, may be present in amounts ranging from 30%-90% (w/w) or thereabouts, with the balance comprising ionophores, ionic additives, and plasticizers in varying ratios.

Sulfate-Sensing Membranes

In some embodiments, to achieve ion selectivity for sulfate ($S_4^{2-}$), the ionophore 1,3-[bis(3-phenylthioureidomethyl)]benzene, 4-(4-bromophenyl)-2,6-diphenylpyrilium perchlorate (BDPP), or a mixture thereof is added to the dissolved matrix material. The matrix material, in some embodiments, may be present in amounts ranging from 30%-90% (w/w) or thereabouts, with the balance comprising ionophores, ionic additives, and plasticizers in varying ratios.

Reference Electrodes

In some embodiments, where metal gates are removed from the transistor structures to yield ISFETs/ChemFETs, one or more reference electrodes are added to the sensor assembly, the reference electrode(s) being configured for placement in (and durability within) the same medium as the ISFETs/ChemFETs (e.g., soil). Traditional reference electrode designs often contain liquids that are prone to drying out, and are typically constructed using glass, further reducing their ruggedness. By contrast, reference electrodes of the present disclosure, using solid-state electrolytes, address these weaknesses. For example, in some embodiments, the reference electrode assembly contains a "frit" to enable ionic transport from the soil to the solid-state electrolyte; the frit materials may be comprised of porous ceramic, glass, or polymeric materials.

Large Reference Electrodes

Figure 9:
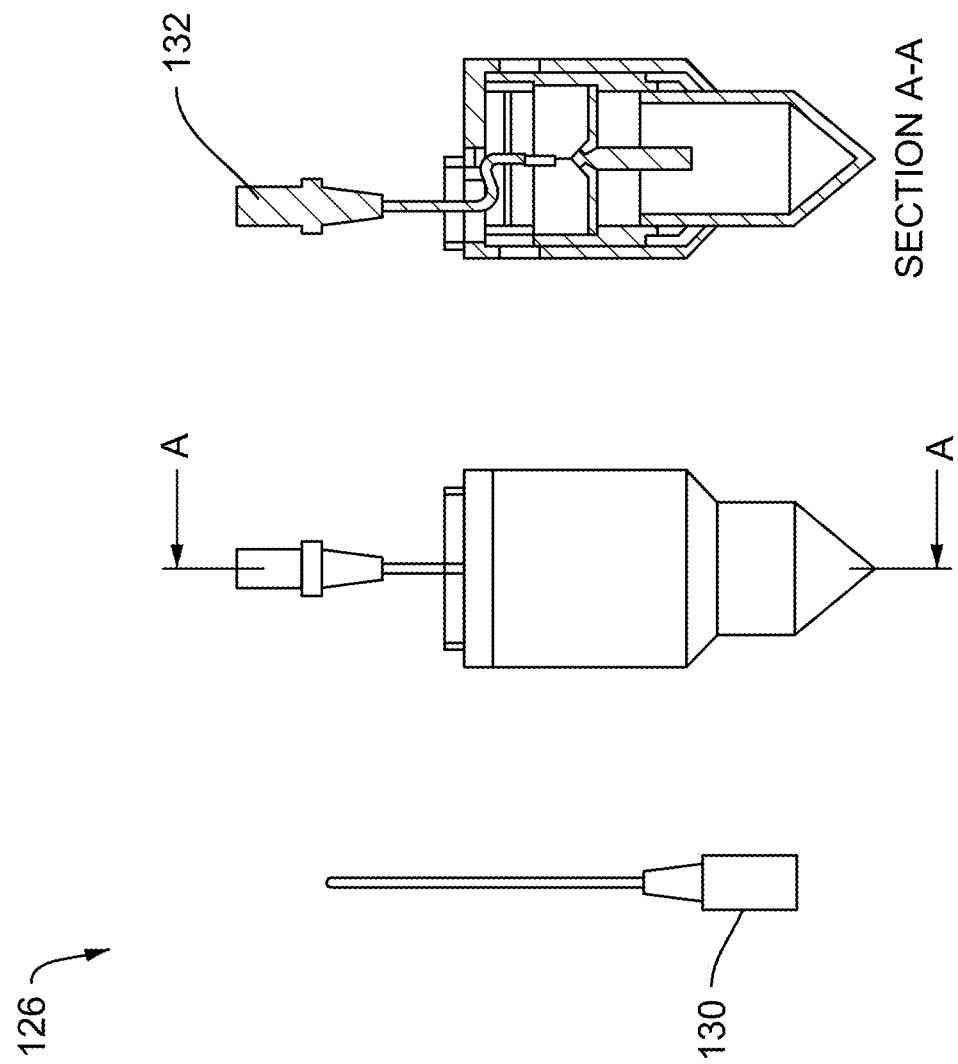
FIG. 9 includes schematic drawings of a large reference electrode assembly, according to an embodiment.
Figure 12:
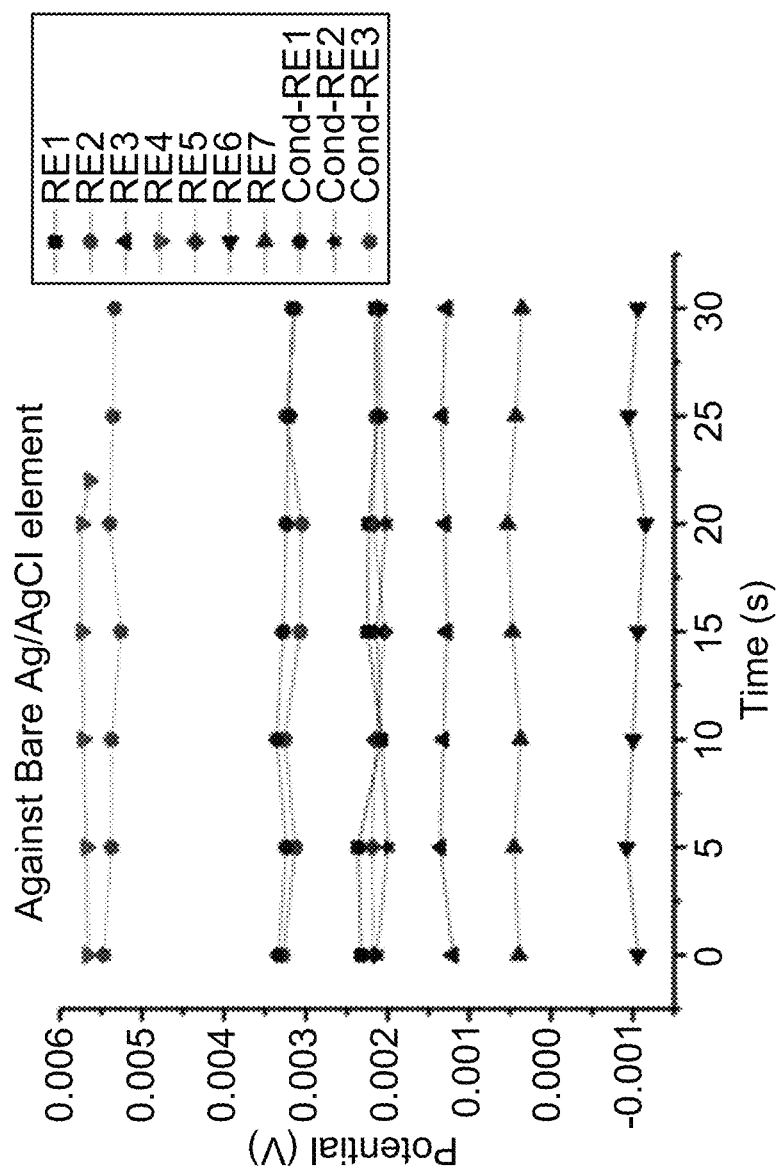
FIG. 12 is a plot showing stability testing data for a reference electrode vs. a silver/silver chloride (Ag/AgCl) reference electrode, according to an embodiment.
Figure 11:
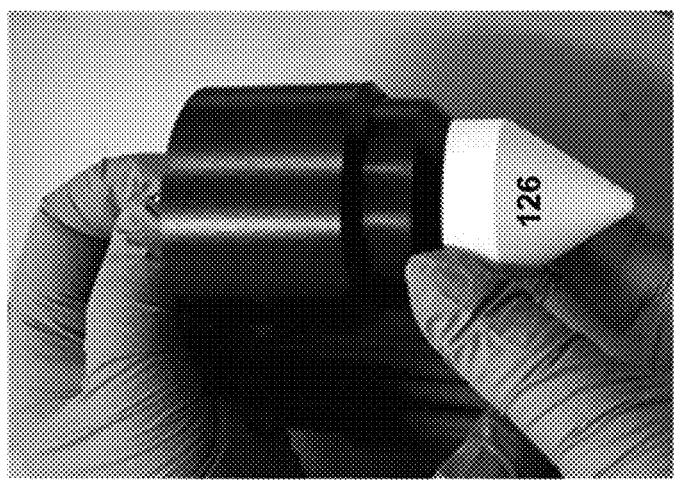
FIG. 11 is a photograph of a large reference electrode, according to an embodiment.

As shown in FIG. 9, a large reference electrode assembly 126, compatible, for example, with the sensor assemblies of FIGS. 2A-2B and FIG. 3, includes a main body portion with a male connector 132 extending therefrom, the male connector 132 configured to connect with (i.e., be received by) a female connector 130. FIG. 11 is a photograph of an assembled large reference electrode 126, compatible, for example, with the sensor assemblies of FIGS. 2A-2B, FIG. 3, or FIGS. 6A-6D, according to an embodiment. Assembled reference electrodes of varying electrolyte composition have been tested against reference Ag/AgCl elements to monitor their stability of the reference potential and to examine potential drift. FIG. 12 is a plot showing comparison data for large reference electrodes ("RE's") vs. a silver/silver chloride (Ag/AgCl) reference electrode, according to an embodiment. As demonstrated by the plot data in FIG. 12, each of the tested reference electrodes (RE1 through RE7 and versions of RE1 through RE3 "conditioned" in an electrolyte storage solution) compared favorably with bare Ag/AgCl reference electrodes. The assembly process for large reference electrodes is provided in the Example Reference Electrode Assembly Process section below.

Small Reference Electrodes

Figure 10:
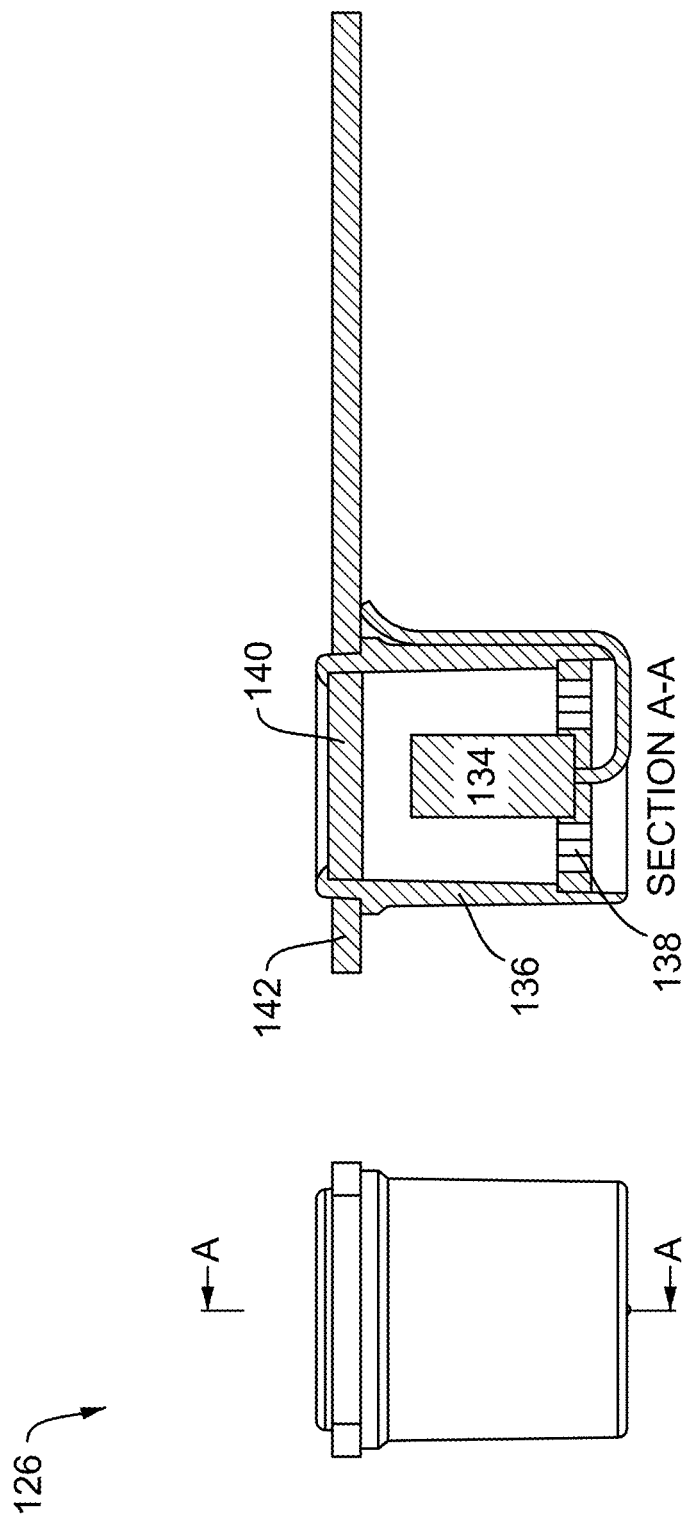
FIG. 10 includes schematic drawings of a small reference electrode, according to an embodiment.
Figure 14:
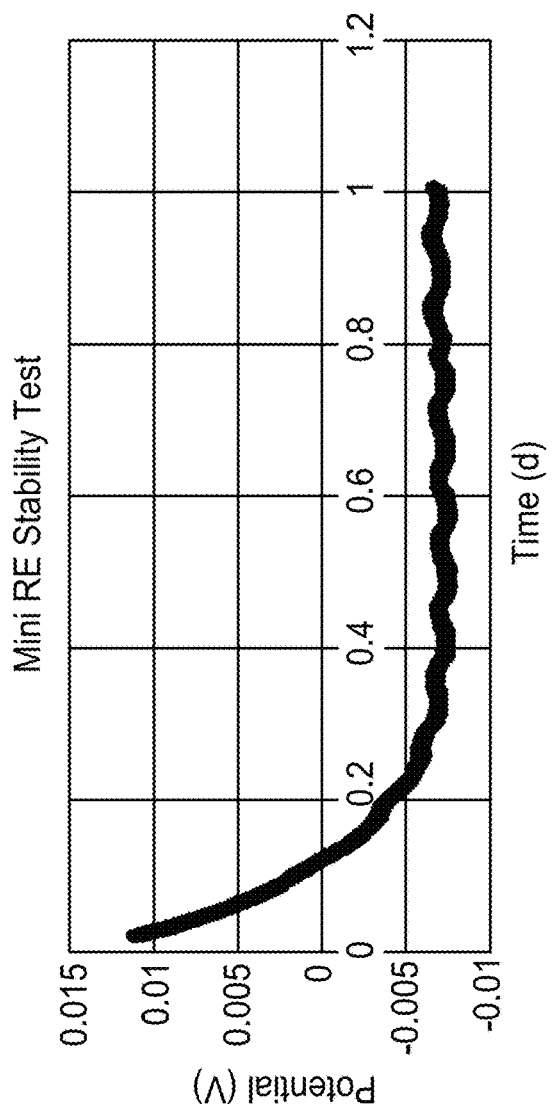
FIG. 14 is a plot showing test data for a small reference electrode, according to an embodiment.
Figure 13:
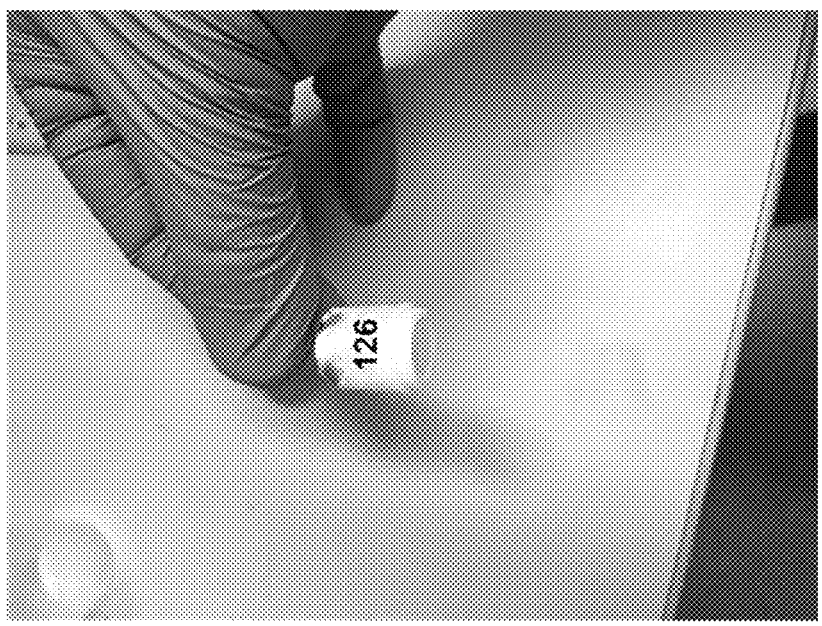
FIG. 13 is a photograph of a small reference electrode, according to an embodiment.

Additional form factors have been developed, including small/miniature ("mini") versions of the solid-state reference electrode. These are typically intended to be located near the sensor arrays, rather than at the tip of the sensor stake. Schematic drawings of a small reference electrode 126, compatible, for example, with the sensor assemblies of FIGS. 4A-4B and FIG. 5. As shown in FIG. 10, a small (or "mini") reference electrode 126 includes a silver (Ag) electrode 134 positioned within a recess formed by sleeve 136 and at least partially supported by an internal cap 138 (which, in some embodiments, is integrally formed with the sleeve 136). A lid 140 is positioned at the top of the recess formed by sleeve 136. A sensor module PCB 142 (e.g., including conductive traces and/or electronics) is mechanically attached to the sleeve 136 (or other components of the reference electrode 126) and is electrically connected to the Ag electrode 134. A photograph of a fully assembled mini reference electrode is provided in FIG. 13. An example of where the mini reference electrode of FIG. 13 may be located relative to the overall sensor assembly can be seen, for example, in FIGS. 4A-4B (reference electrode 126—in each instance of a sensor block, multiple of which may be included in an overall sensor assembly) and in FIG. 5 (reference electrodes 126—in each instance of a sensor block 100). FIG. 14 is a plot showing stability testing data for a small reference electrode, according to an embodiment. As demonstrated by the plot data in FIG. 12, there is a "settling" or "equilibration" period (over the first ~0.3 days) during which the potential being measured by the reference electrode decreases (e.g., asymptotically) until it approaches a steady-state value (in this case, about −0.003 V). This "equilibration" period may be taken into account when processing sensor signals of the sensor assembly, for example by excluding or disregarding data collected during the "equilibration" period, or making adjustments thereto (e.g., based on a time at which the particular data point was measured/detected).

Example Reference Electrode Assembly Process

In some embodiments, a reference electrode includes a housing, a ceramic frit, a Ag/AgCl element, and a solid electrolyte comprising "Plaster of Paris" ($CaSO_4 \cdot 0.5\ H_2O$) and NaCl. To assemble the reference electrode, the ceramic frit (e.g., made of a metal oxide such as alumina ($Al_2O_3$)) is affixed to the reference electrode housing, for example using an epoxy (in which case the assembly, one epoxied, is allowed to cure overnight). The Ag/AgCl element is secured to the reference electrode cap using a small quantity of epoxy to the upper face (where the bare Ag wire originates)

of the Ag/AgCl element. The bare Ag wire protrudes from the cap and is affixed to a copper (or similar metal) wire using a solder or crimped connection. The result of this assembly step is the Ag/AgCl element, which is epoxied to the reference electrode cap, which in turn is connected to copper or a similarly conductive wire.

After the ceramic frit is secured to the reference electrode body, a solid electrolyte mixture of deionized water, "Plaster of Paris" ($CaSO_4 \cdot 0.5 \, H_2O$), and NaCl is poured into the main cavity in the reference electrode housing. Within about one minute, the Ag/AgCl element from the cap-Ag/AgCl assembly is submerged into the solid electrolyte mixture prior to solidification. The solidification process of the solid electrolyte material is completed within about approximately twenty minutes. The solid electrolyte composition can be varied based on the targeted soil under analysis.

Upon installation of the Ag/AgCl element into the solid electrolyte, the cap is epoxied or otherwise secured to the main reference electrode body, thereby completing the assembly of the reference electrode.

Sensor Arrays

Figure 16:
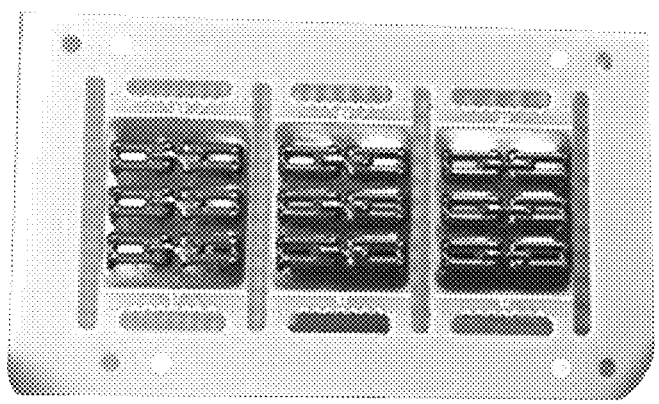
FIG. 16 is a photograph of a set of encapsulated six-sensor array boards, according to an embodiment.
Figure 15:
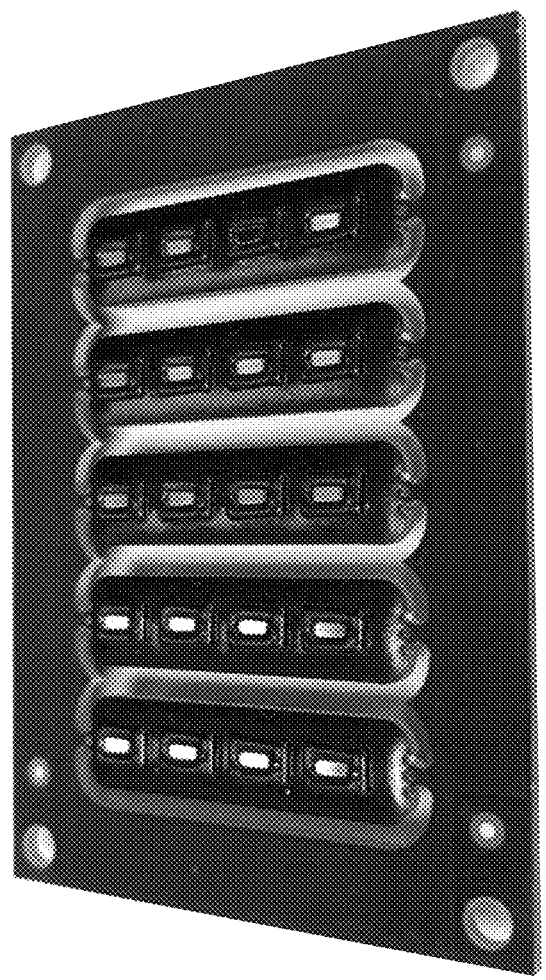
FIG. 15 is a photograph of a set of encapsulated four-sensor array boards, according to an embodiment.

FIG. 15 is a photograph of five encapsulated four-sensor arrays (i.e., four sensors arranged in a single row per array, with five arrays on a single board), according to an embodiment. FIG. 16 is a photograph of a set of three encapsulated six-sensor array boards, according to an embodiment.

ISFET Interface Circuit

Figure 17:
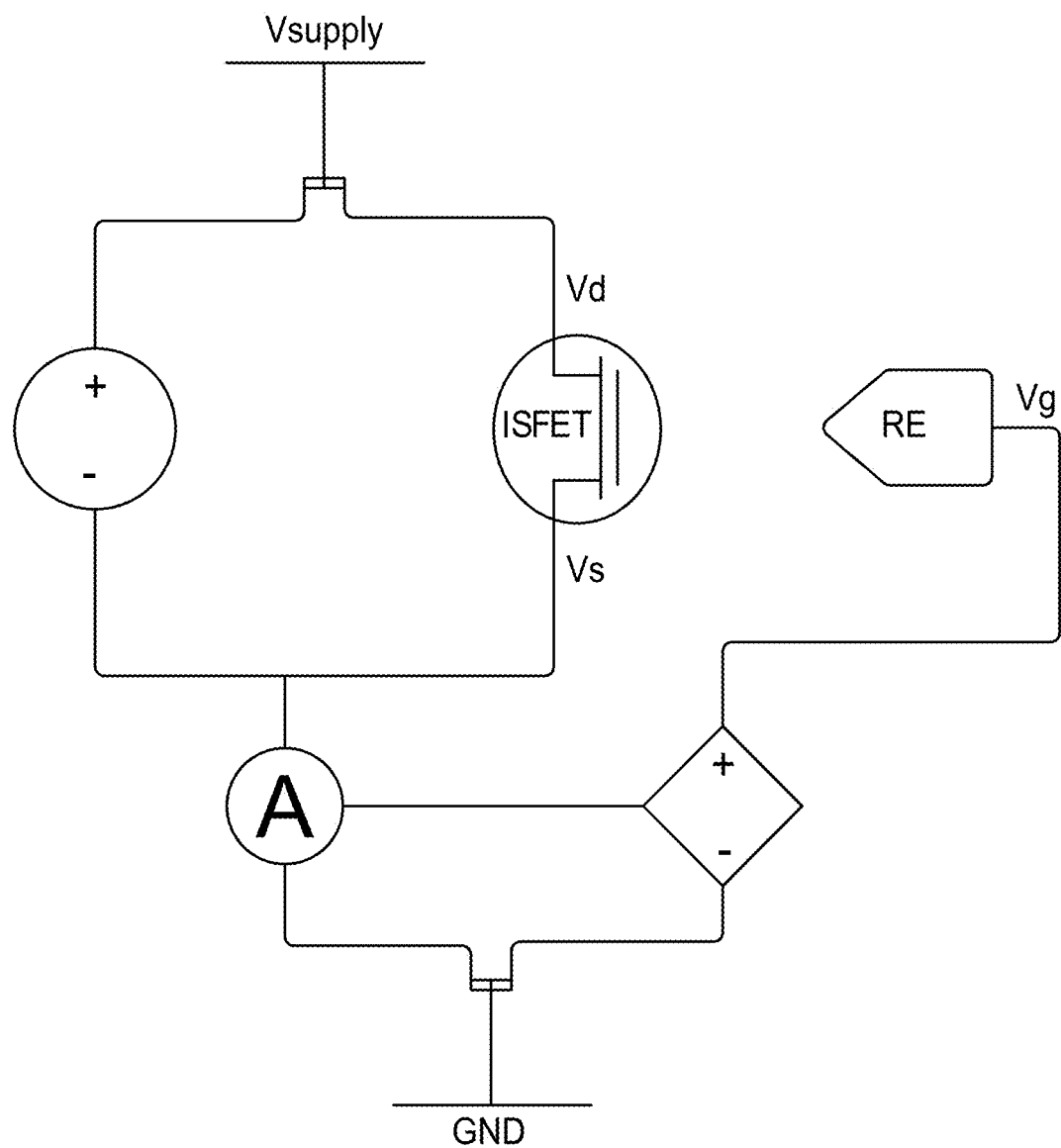
FIG. 17 is an ISFET interface circuit, according to an embodiment.
Figure 18:
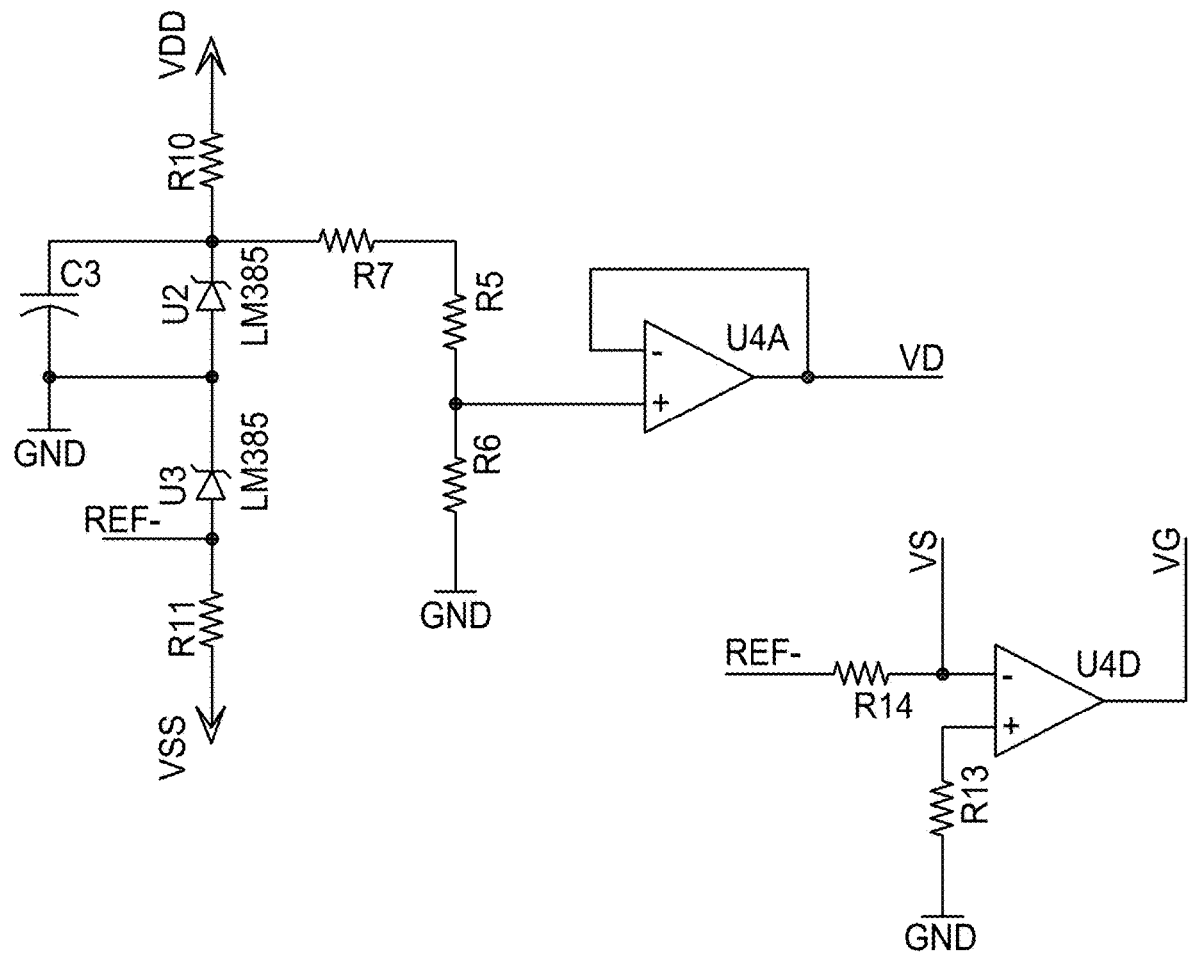
FIG. 18 is an example implementation of the ISFET interface circuit of FIG. 17.

In some embodiments, the ISFET device operates under a constant-voltage, constant-current bias scheme. A voltage source enforces a constant source-drain voltage $V_{ds}$ ($V_d - V_s$), for example approximately 0.3 V. A feedback loop senses the source-drain current through the ISFET (Ids) and adjusts the gate voltage $V_g$, until the Ids reaches a specified current, in some embodiments approximately 25 uA. The gate-source voltage $V_{gs}$ ($V_g - V_s$) is then measured and represents the output of the sensor. An ISFET interface circuit schematic diagram and example implementation are shown in FIG. 17 and FIG. 18, respectively. In FIG. 17 a voltage source ($V_{supply}$) defines the ISFET $V_{ds}$ potential. An ammeter senses the current flowing through the voltage source and the ISFET. Based on the output of the ammeter, a current controlled voltage source adjusts the gate voltage, $V_g$, to reach the desired ISFET current. In FIGS. 18, U2 and U3 provide stable positive and negative reference voltages for biasing the ISFET. The resistors R5, R6, and R7 act as a voltage divider to generate the necessary Vas. The operational amplifier U4A buffers the $V_d$ voltage and provides a low output impedance to drive the ISFET. The resistor R14 is the current sensing element, and together with operational amplifier U4D, creates the current controlled voltage source that drives the reference electrode (RE) potential. In stable sensing operation, $V_s$ will be approximately 0 V and the output of the sensor can be read as $V_g$.

ISFET Multiplexing

Figure 19:
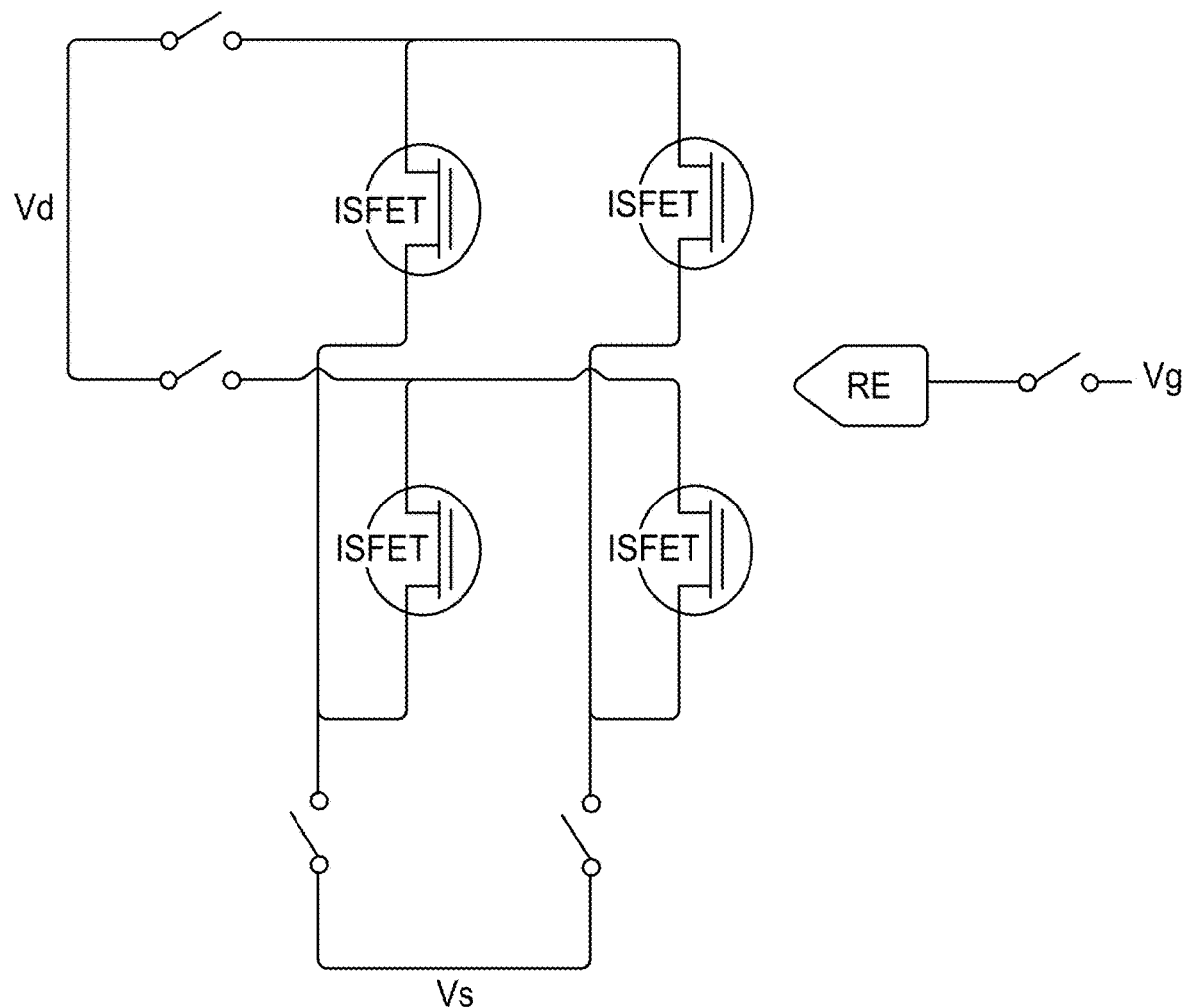
FIG. 19 is an ISFET multiplexing circuit, according to an embodiment.

Several ISFET devices may be multiplexed into a single interface circuit through standard multiplexing techniques. Here, several low on-resistance (Ron) single-pole-single-throw solid state switches are used to switch rows connected to drains of ISFET devices and columns connected to sources of ISFET devices. Optionally, the reference electrode may also be selectively connected to the interface circuit through similar switches. These switches may be discrete devices or integrated into a single package. An example ISFET multiplexing circuit is shown in FIG. 19.

Sensor Calibration (Field and Lab Studies)

Figure 30:
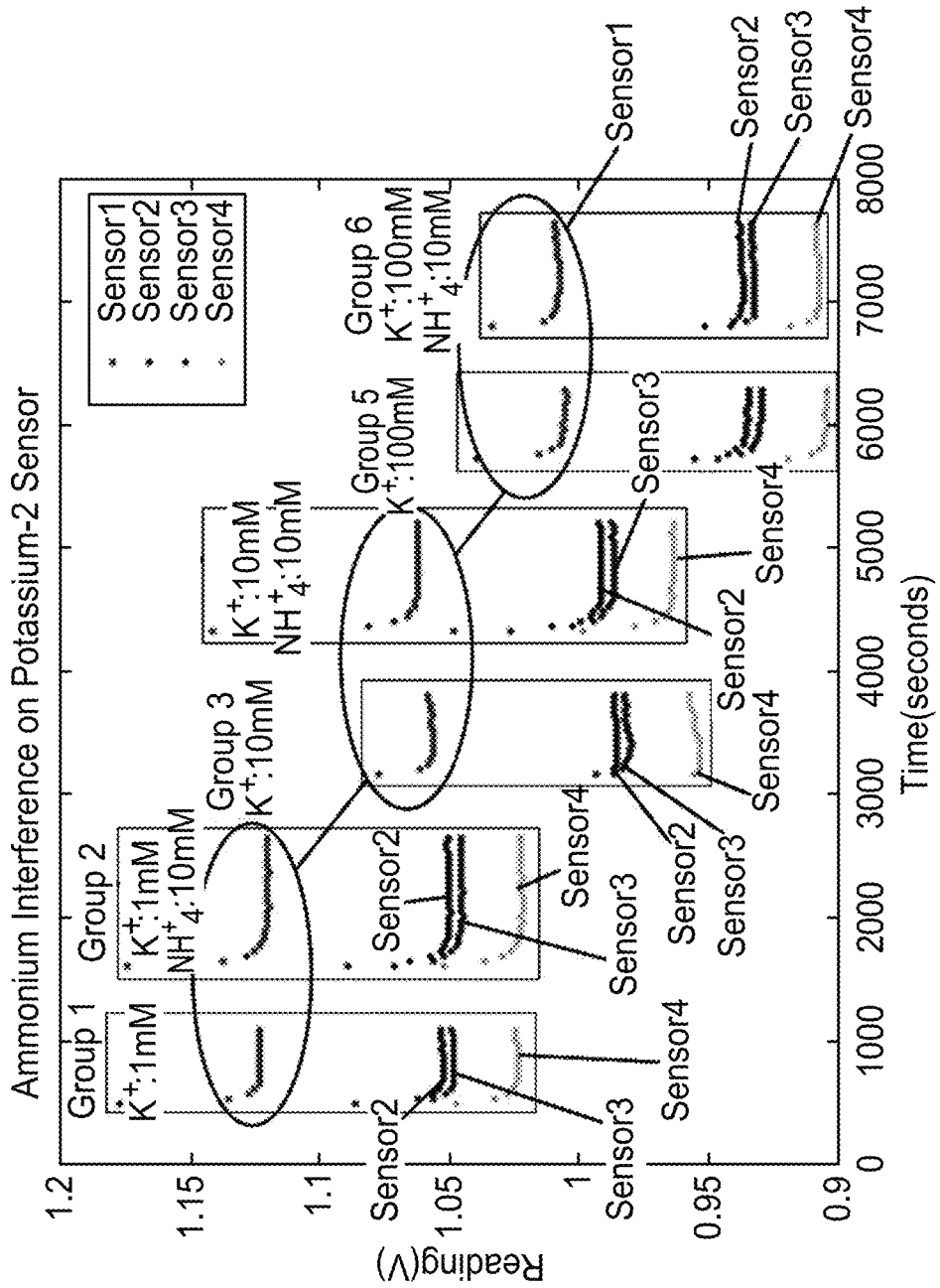
FIG. 30 is a plot showing the effect of ammonium on the performance of potassium sensors, according to an embodiment.
Figure 31:
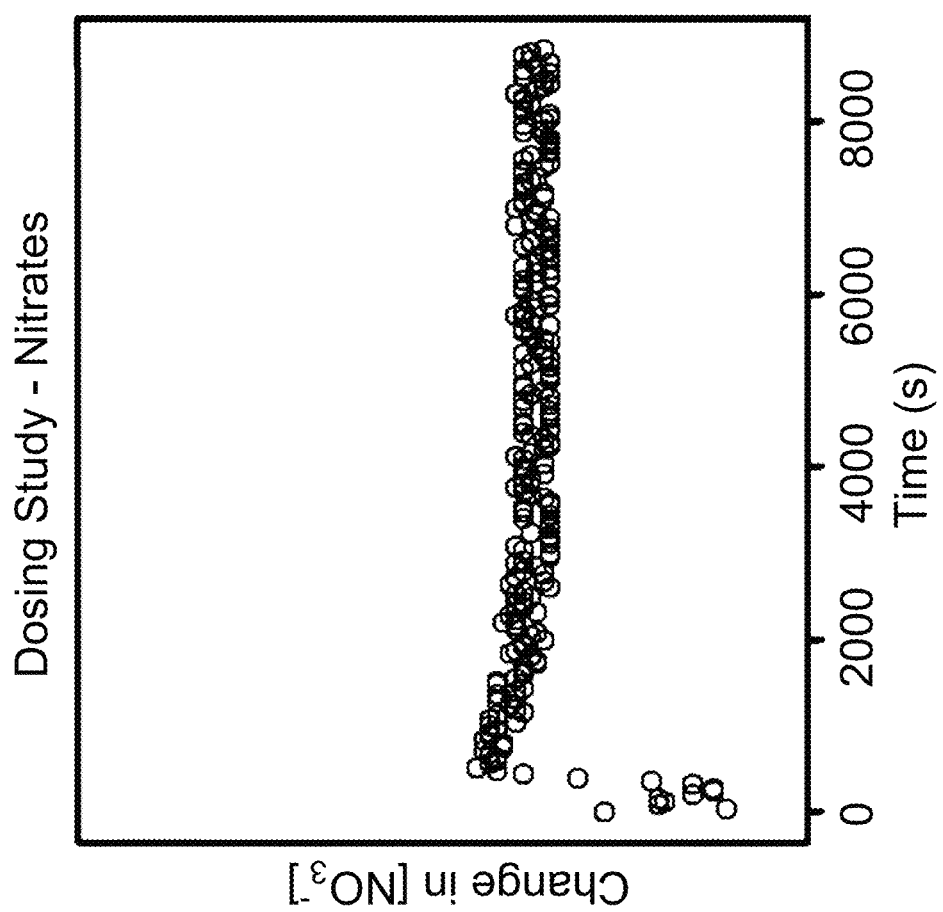
FIG. 31 is a plot showing a dynamic response of a nitrate sensor to an applied dose of nitrate solution, in accordance with some embodiments.

Calibration data for pH ISFETs and nitrate, phosphate, and potassium ChemFETs can be seen in FIGS. 20-23, respectively. Testing has been conducted to assess the selectivity of the ChemFETs toward interfering ions. In the case of nitrate sensors, they have been tested against anions such as sulfates (FIG. 24), carbonates (FIG. 25), and chloride ions (FIG. 26). The potassium sensors have been tested against common cations found in soil, such as sodium (FIG. 27), calcium (FIG. 28), magnesium (FIG. 29), and ammonium (FIG. 30). Both sensors have demonstrated strong selectivity toward the ion of interest (e.g. nitrate, potassium) and reject interfering ions. Tests have been performed to test the dynamic response of sensors to doses of solutions containing the ion of interest in soil. An example of this study conducted in sand is shown in FIG. 31. Data collected from field studies with the sensor stakes has been compared to lab-tested samples. Most results are within 10 ppm of the lab-derived results.

Figure 20:
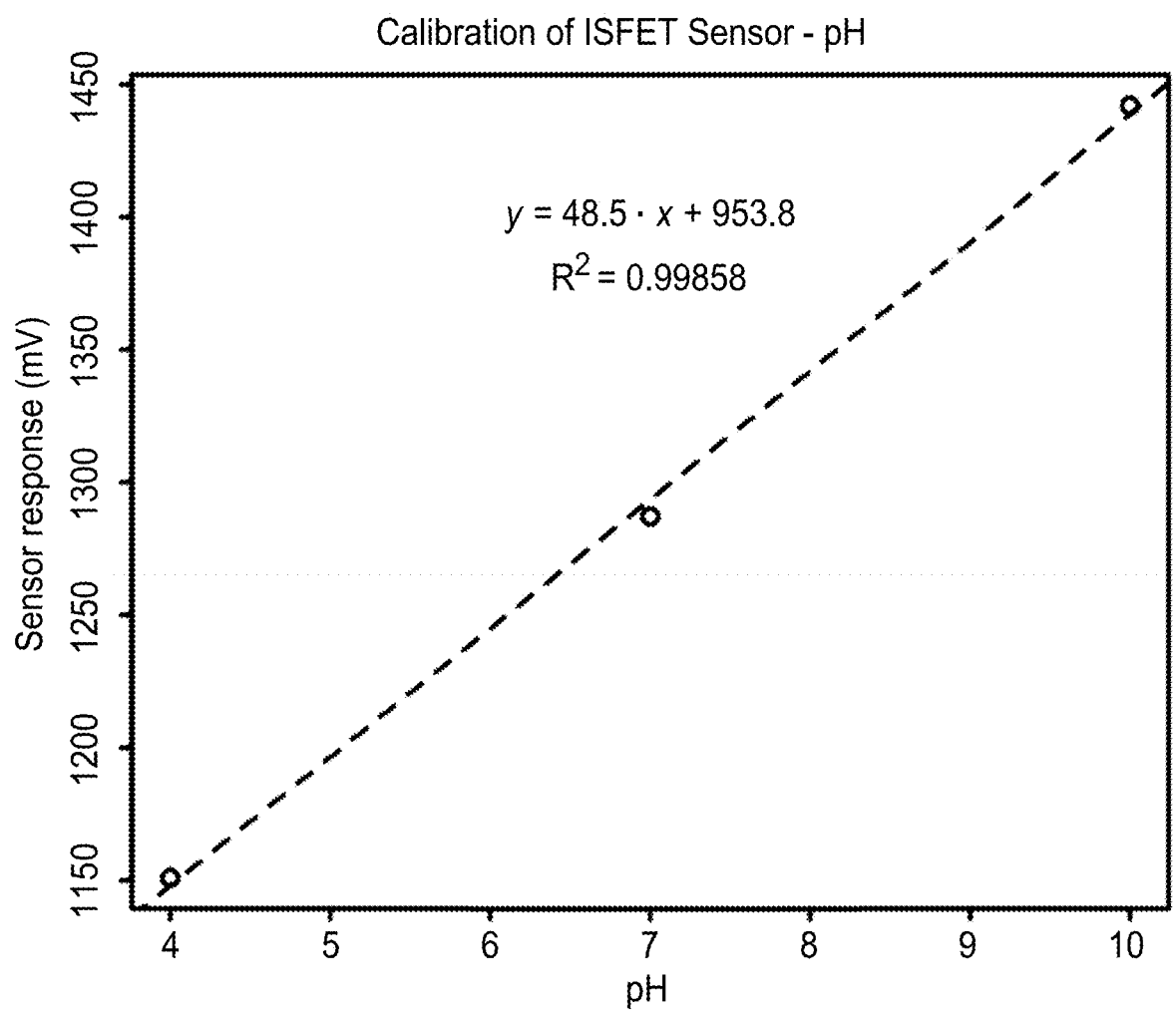
FIG. 20 is a plot showing calibration data for a pH ISFET sensor, according to an embodiment.

FIG. 20 is a plot showing calibration data for a pH ISFET sensor, according to an embodiment. During calibration, three measurements of the sensor response (in millivolts, mV) were taken, in solution, at three different associated pH levels (in this case, pH values of about 4, about 7, and about 10). The sensor response data was plotted, and a line of best fit was drawn (in this case, y=48.5x+953.8), and a coefficient of determination ($R^2$) was calculated (in this case, $R^2$=0.99858).

Figure 21:
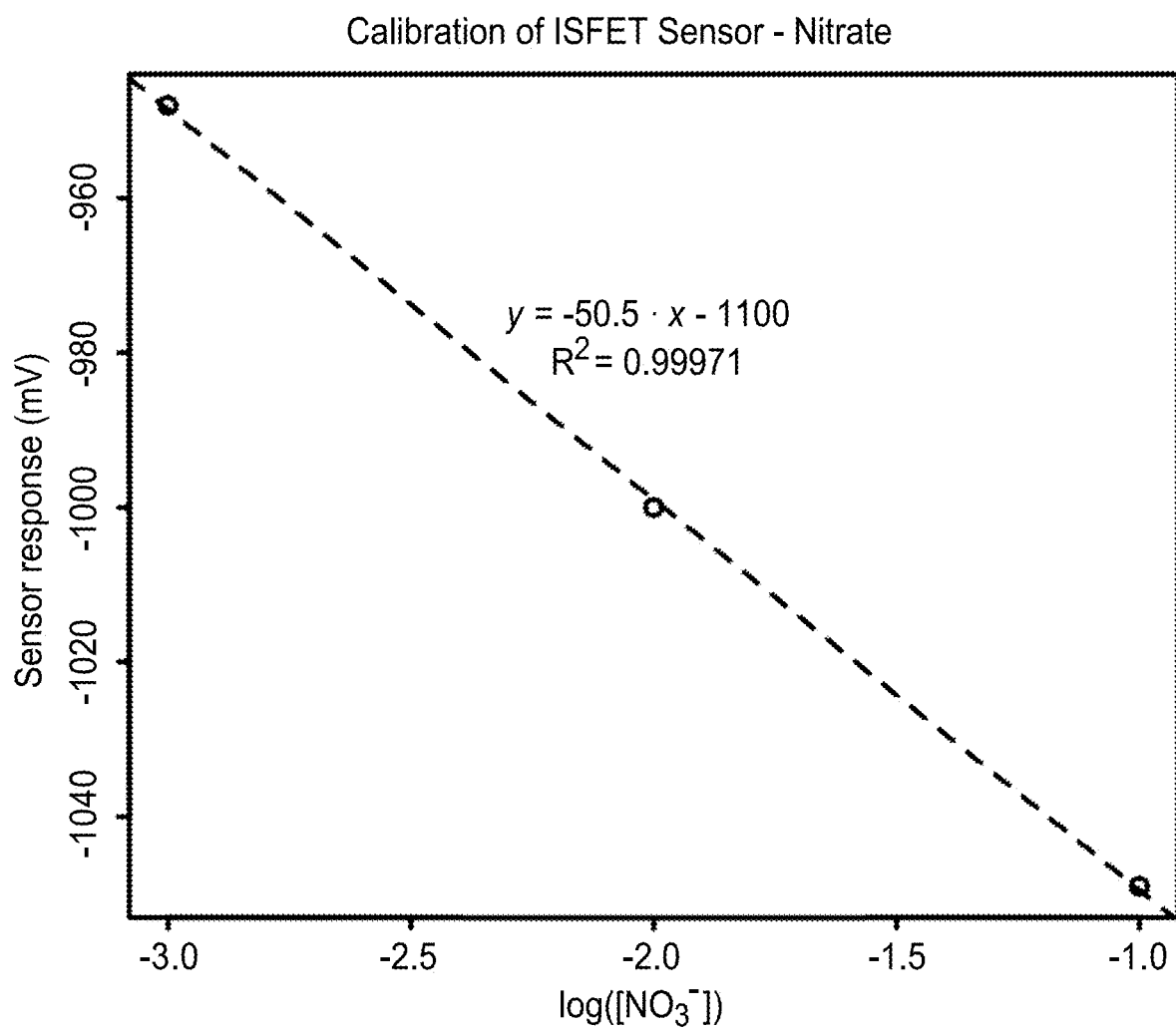
FIG. 21 is a plot showing calibration data for a nitrate ISFET sensor, according to an embodiment.

FIG. 21 is a plot showing calibration data for a nitrate ISFET sensor, according to an embodiment. During calibration, three measurements of the sensor response (in mV) were taken, in solution, at three different values of log ([$NO_3^-$]) (in this case, log([$NO_3^-$]) values of about −3.0, about −2.0, and about −1.0). The sensor response data was plotted, and a line of best fit was drawn (in this case, y=−50.5x−1100), and a coefficient of determination ($R^2$) was calculated (in this case, $R^2$=0.99971).

Figure 22:
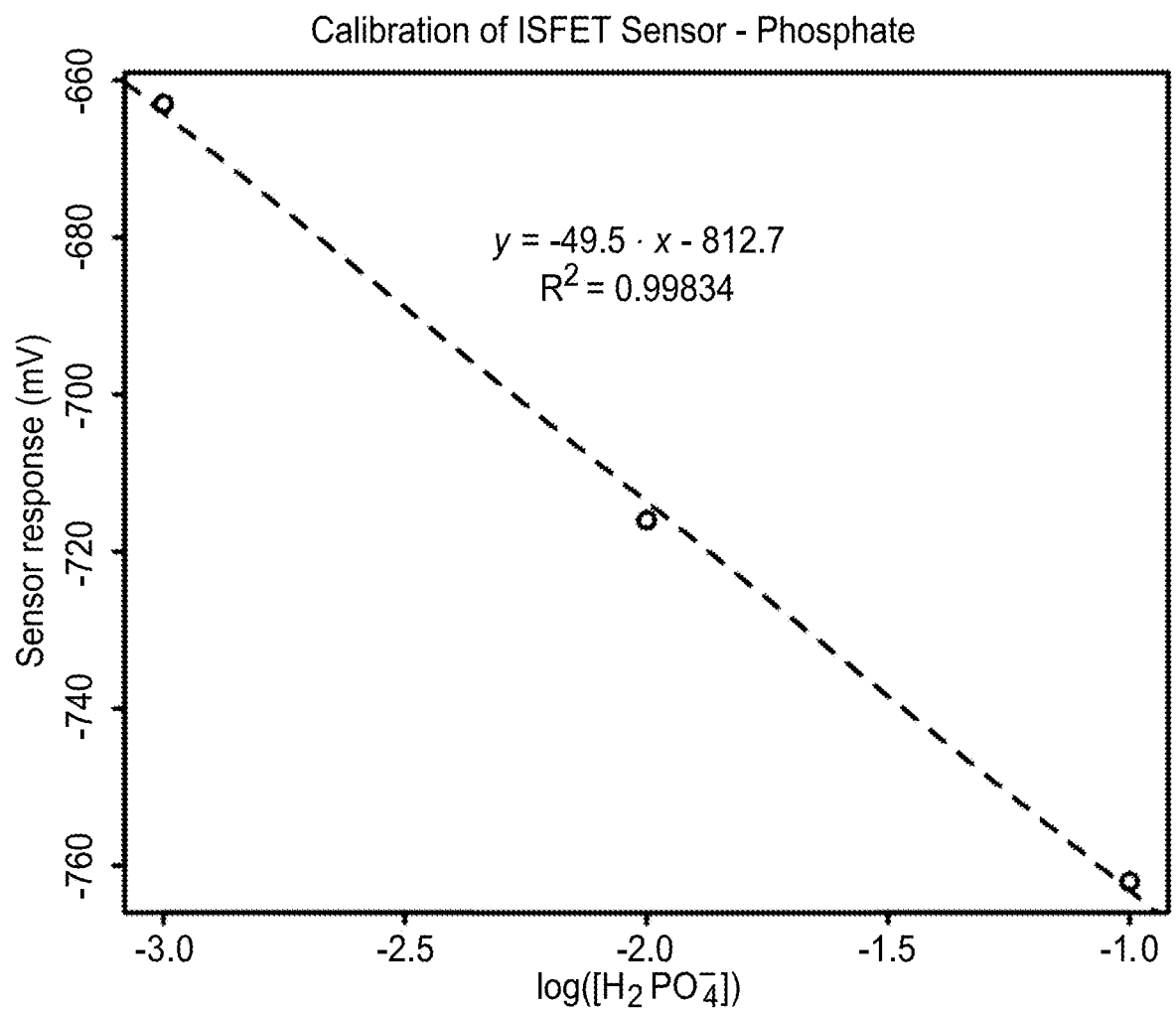
FIG. 22 is a plot showing calibration data for a phosphate ISFET sensor, according to an embodiment.

FIG. 22 is a plot showing calibration data for a phosphate ISFET sensor, according to an embodiment. During calibration, three measurements of the sensor response (in mV) were taken, in solution, at three different values of log ([$H_2PO_4^-$]) (in this case, log([$H_2PO_4^-$]) values of about −3.0, about −2.0, and about −1.0). The sensor response data was plotted, and a line of best fit was drawn (in this case, y=−49.5x−812.7), and a coefficient of determination ($R^2$) was calculated (in this case, $R^2$=0.99834).

Figure 23:
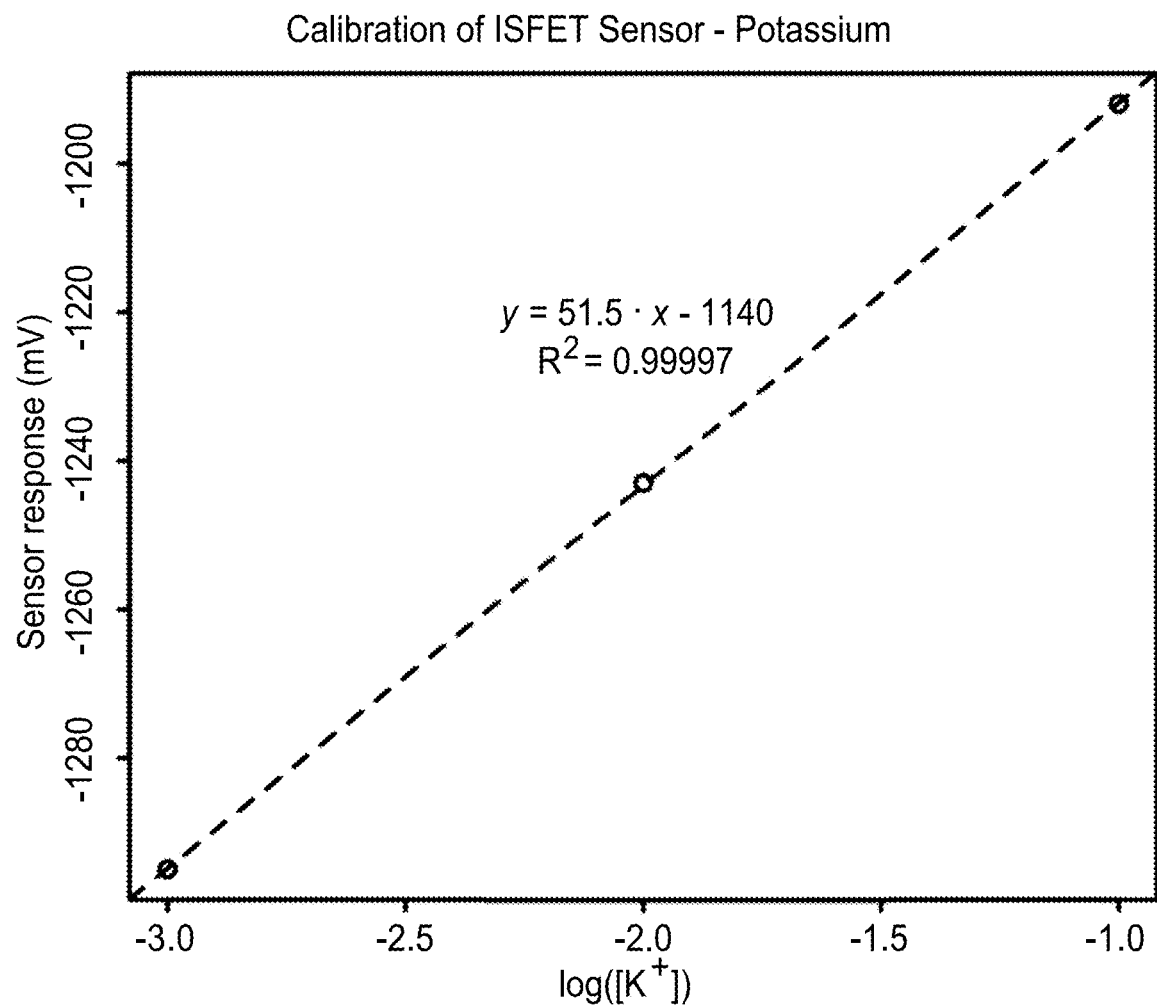
FIG. 23 is a plot showing calibration data for a potassium ISFET sensor, according to an embodiment.

FIG. 23 is a plot showing calibration data for a potassium ISFET sensor, according to an embodiment. During calibration, three measurements of the sensor response (in mV) were taken, in solution, at three different values of log([$K^+$]) (in this case, log([$K^+$]) values of about −3.0, about −2.0, and about −1.0). The sensor response data was plotted, and a line of best fit was drawn (in this case, y=51.5x−1140), and a coefficient of determination ($R^2$) was calculated (in this case, $R^2$=0.99997).

Sensitivity of Sensors to Contaminants

Figure 24:
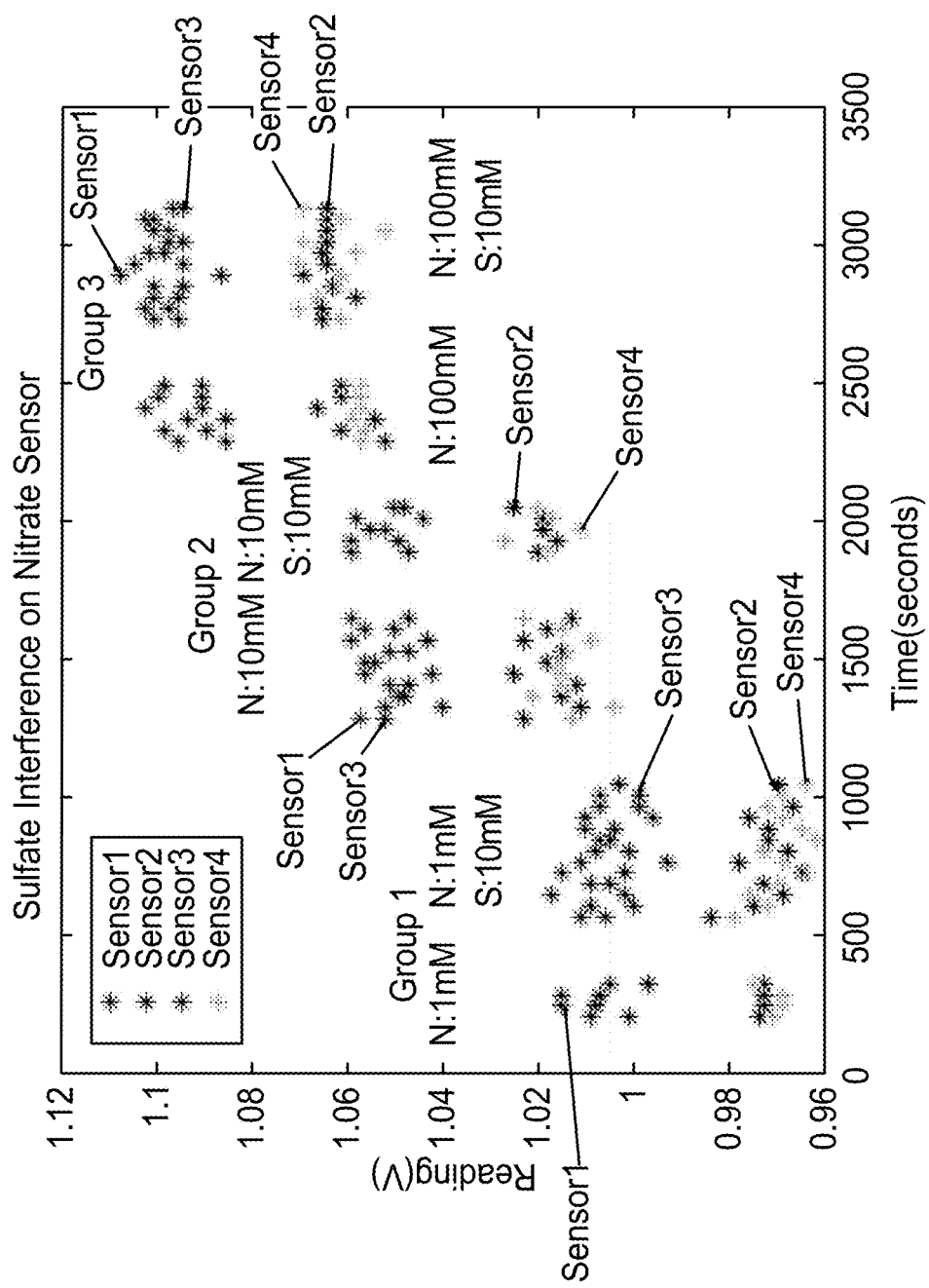
FIG. 24 is a plot showing the effect of sulfate on the performance of nitrate sensors, according to an embodiment.

FIG. 24 is a plot showing the effect of sulfate, as a potential contaminant, on the performance of nitrate sensors (using a Ag/AgCl reference electrode), according to an embodiment. As shown in FIG. 24, side-by-side comparisons of sequential sensor readings (using four distinct sensors, Sensors 1 through 4) for nitrate ($NO_3^-$) alone (left portion of each grouping) and nitrate in the presence of sulfate (right portion of each grouping) are shown for three different ratios of nitrate to sulfate (i.e., Grouping 1=1 mM nitrate, 10 mM sulfate; Grouping 2=10 mM nitrate, 10 mM sulfate; Grouping 3=100 mM nitrate, 10 mM sulfate). The data in FIG. 24 shows that the nitrate sensor performance was stable even in the presence of sulfate.

Figure 25:
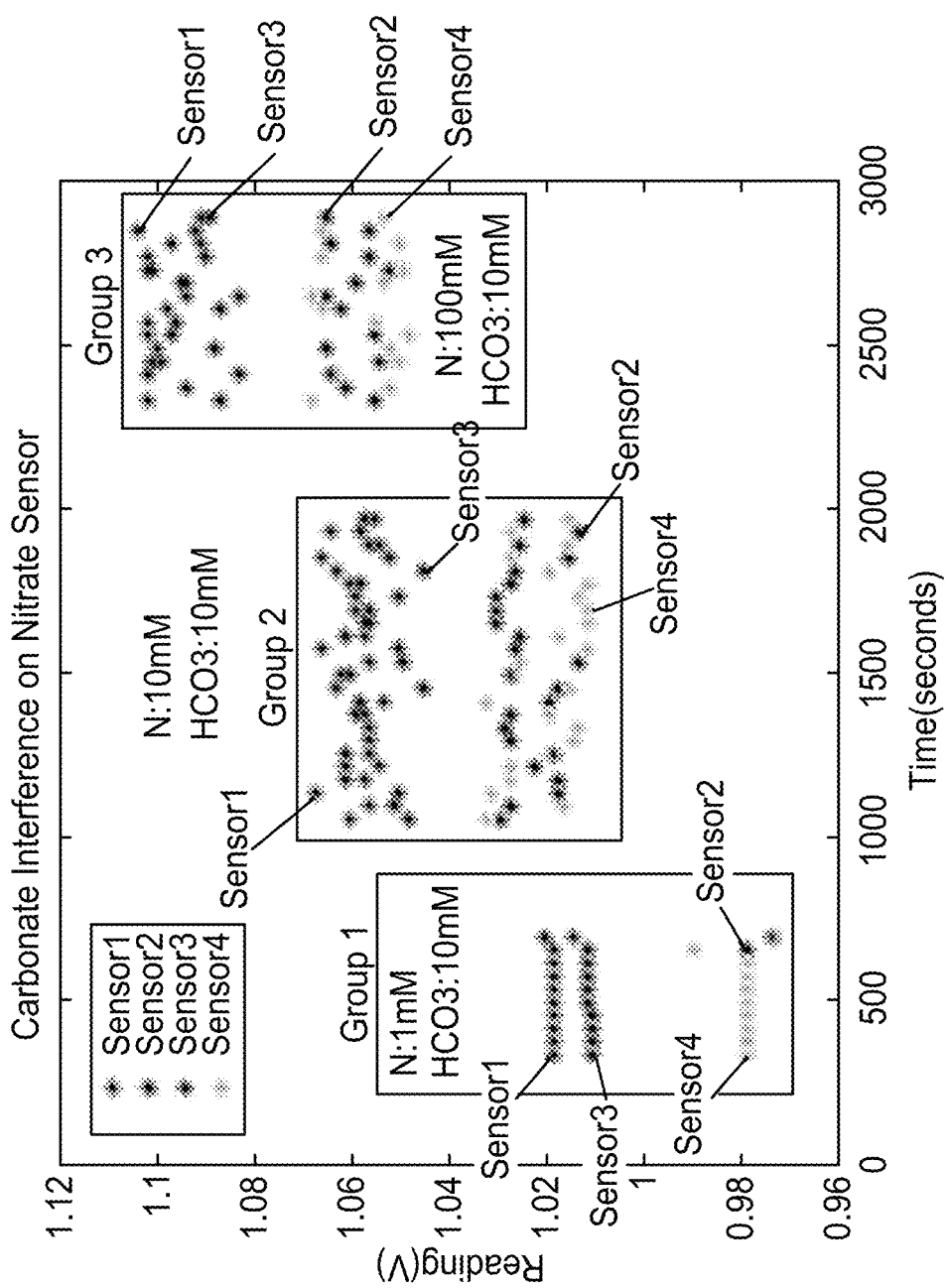
FIG. 25 is a plot showing the effect of carbonate on the performance of nitrate sensors, according to an embodiment.
Figure 26:
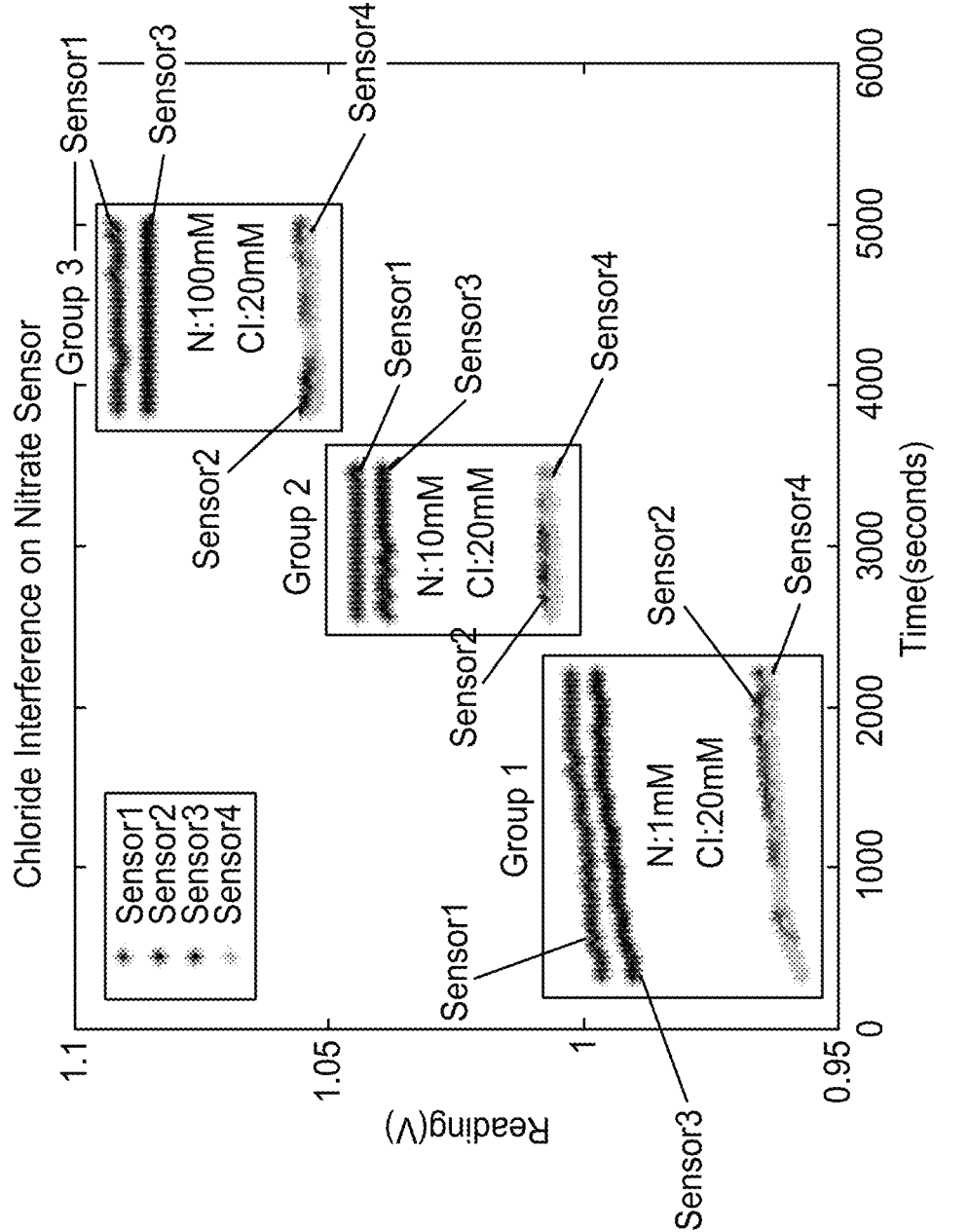
FIG. 26 is a plot showing the effect of chloride on the performance of nitrate sensors, according to an embodiment.

FIG. 25 is a plot showing the effect of carbonate, as a potential contaminant, on the performance of nitrate sensors (using a Ag/AgCl reference electrode), according to an embodiment. As shown in FIG. 25, sequential sensor readings (using four distinct sensors, Sensors 1 through 4) for nitrate in the presence of carbonate ($CO_3^2$) are shown for three different ratios of nitrate to $CO_3^{2-}$ (i.e., Grouping 1=1 mM nitrate, 10 mM carbonate; Grouping 2=10 mM nitrate, 10 mM carbonate; Grouping 3=100 mM nitrate, 10 mM carbonate). The data in FIG. 25 shows that the nitrate sensor performance was stable (e.g., Grouping 1, showing negligible/near-zero variation in voltage) or substantially stable (e.g., Groupings 2 and 3, showing variation in voltage of about 0.02-0.04 V), even in the presence of carbonate.

FIG. 26 is a plot showing the effect of chloride, as a potential contaminant, on the performance of nitrate sensors (using a Ag/AgCl reference electrode), according to an embodiment. As shown in FIG. 26, sequential sensor readings (using four distinct sensors, Sensors 1 through 4) for nitrate in the presence of chloride are shown for three different ratios of nitrate to chloride (i.e., Grouping 1=1 mM nitrate, 20 mM chloride; Grouping 2=10 mM nitrate, 20 mM chloride; Grouping 3=100 mM nitrate, 20 mM chloride). The data in FIG. 26 shows that the nitrate sensor performance was stable (e.g., Groupings 2 and 3, showing negligible/near-zero variation in voltage) or substantially stable (e.g., Grouping 1, showing variation in voltage of about 0.02 V), even in the presence of chloride.

Figure 27:
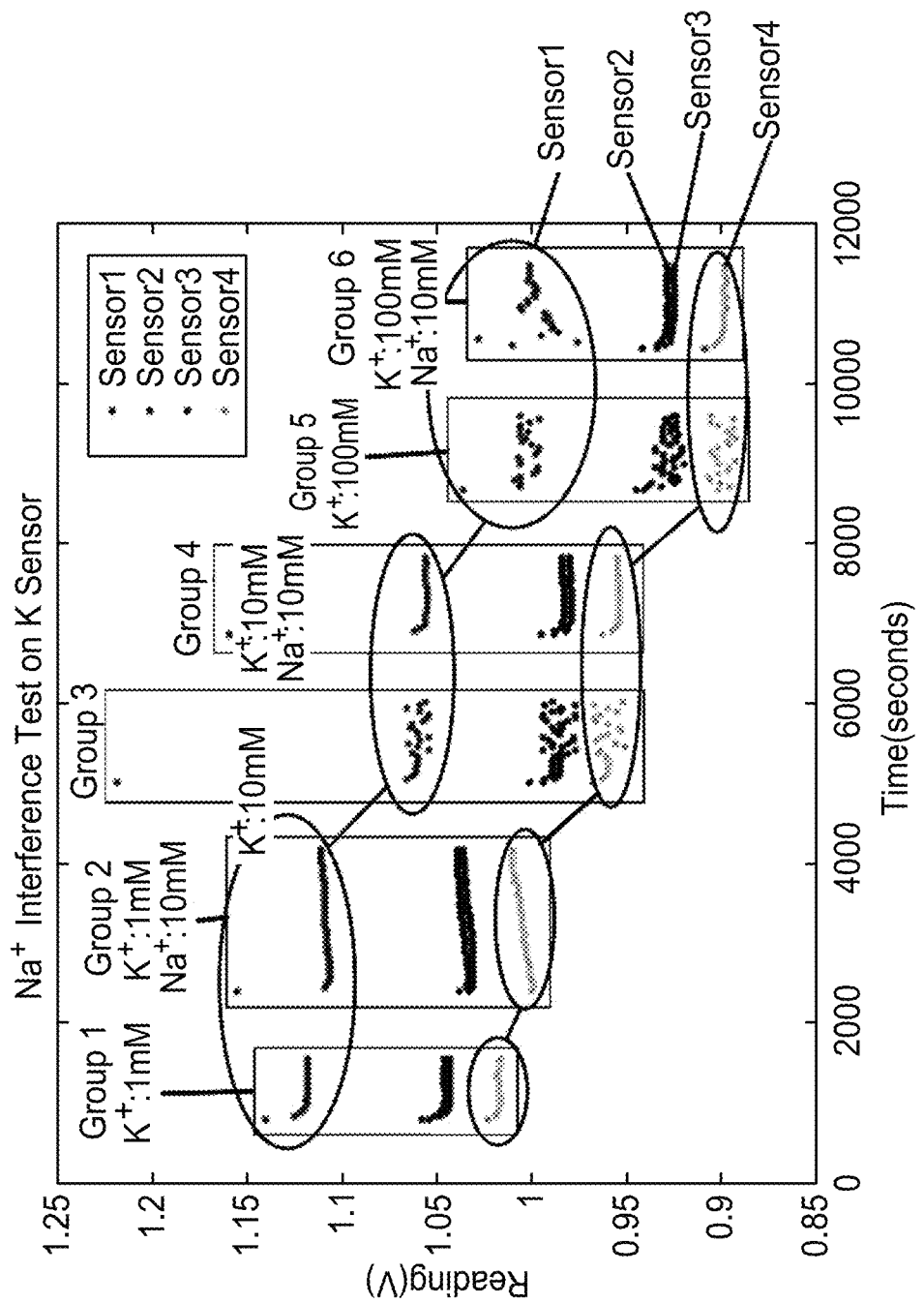
FIG. 27 is a plot showing the effect of sodium on the performance of potassium sensors, according to an embodiment.

FIG. 27 is a plot showing the effect of sodium ions ($Na^+$), as a potential contaminant, on the performance of potassium sensors, according to an embodiment. As shown in FIG. 27, sequential sensor readings (using four distinct sensors, Sensors 1 through 4) for potassium in the presence of sodium are shown for six different ratios of potassium to sodium (i.e., Grouping 1=1 mM potassium, 0 mM sodium; Grouping 2=1 mM potassium, 10 mM sodium; Grouping 3=10 mM potassium, 0 mM sodium; Grouping 4=10 mM potassium, 10 mM sodium; Grouping 5=100 mM potassium, 0 mM sodium; Grouping 6=100 mM potassium, 10 mM sodium). The data in FIG. 27 shows that the potassium sensor performance was stable or substantially stable, even in the presence of sodium.

Figure 28:
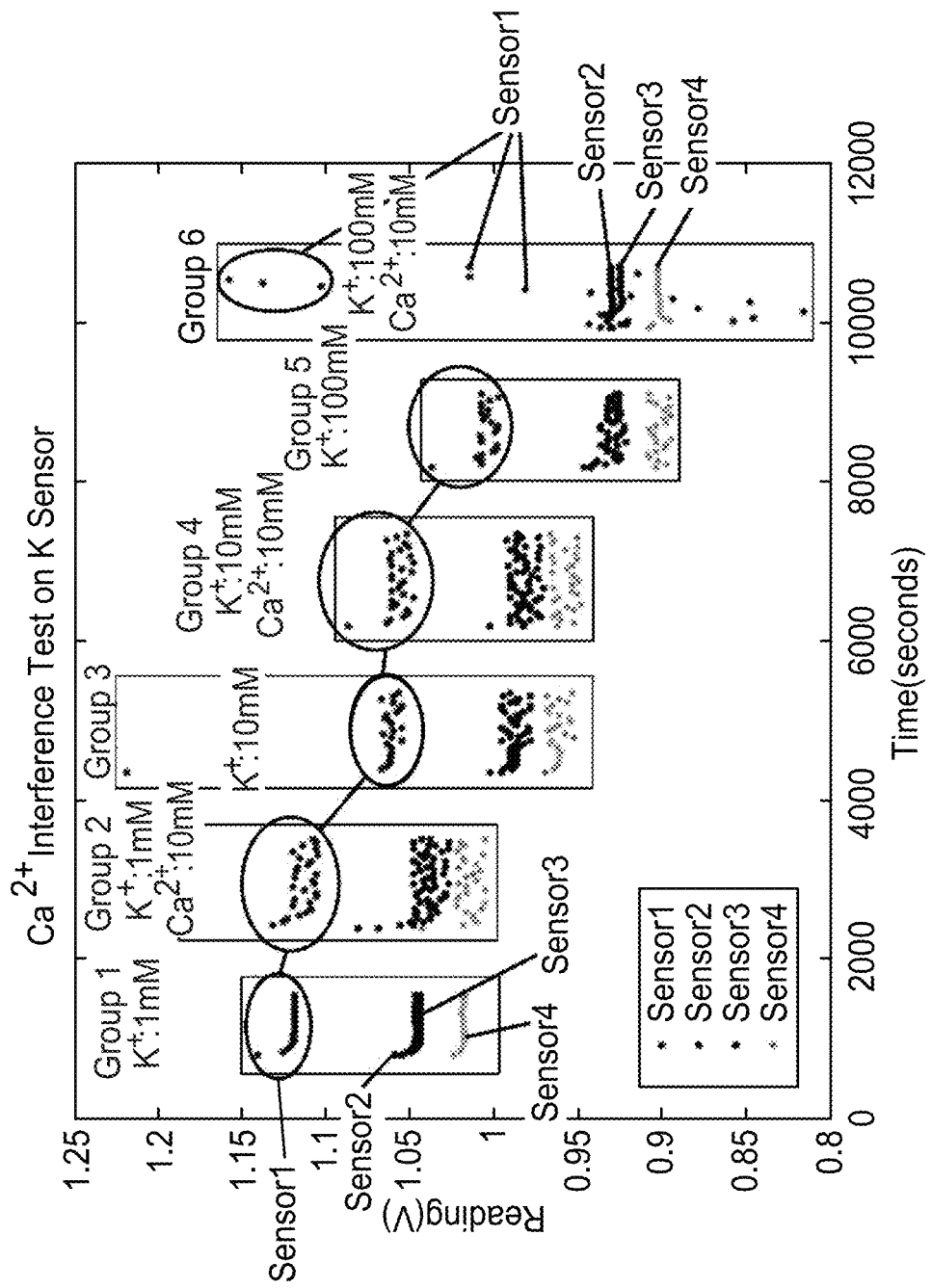
FIG. 28 is a plot showing the effect of calcium on the performance of potassium sensors, according to an embodiment.

FIG. 28 is a plot showing the effect of calcium ions ($Ca^{2+}$), as a potential contaminant, on the performance of potassium sensors, according to an embodiment. As shown in FIG. 28, sequential sensor readings (using four distinct sensors, Sensors 1 through 4) for potassium in the presence of calcium are shown for six different ratios of potassium to calcium (i.e., Grouping 1=1 mM potassium, 0 mM calcium; Grouping 2=1 mM potassium, 10 mM calcium; Grouping 3=10 mM potassium, 0 mM calcium; Grouping 4=10 mM potassium, 10 mM calcium; Grouping 5=100 mM potassium, 0 mM calcium; Grouping 6=100 mM potassium, 10 mM calcium). The data in FIG. 27 shows that the potassium sensor performance was stable or substantially stable, even in the presence of calcium.

Figure 29:
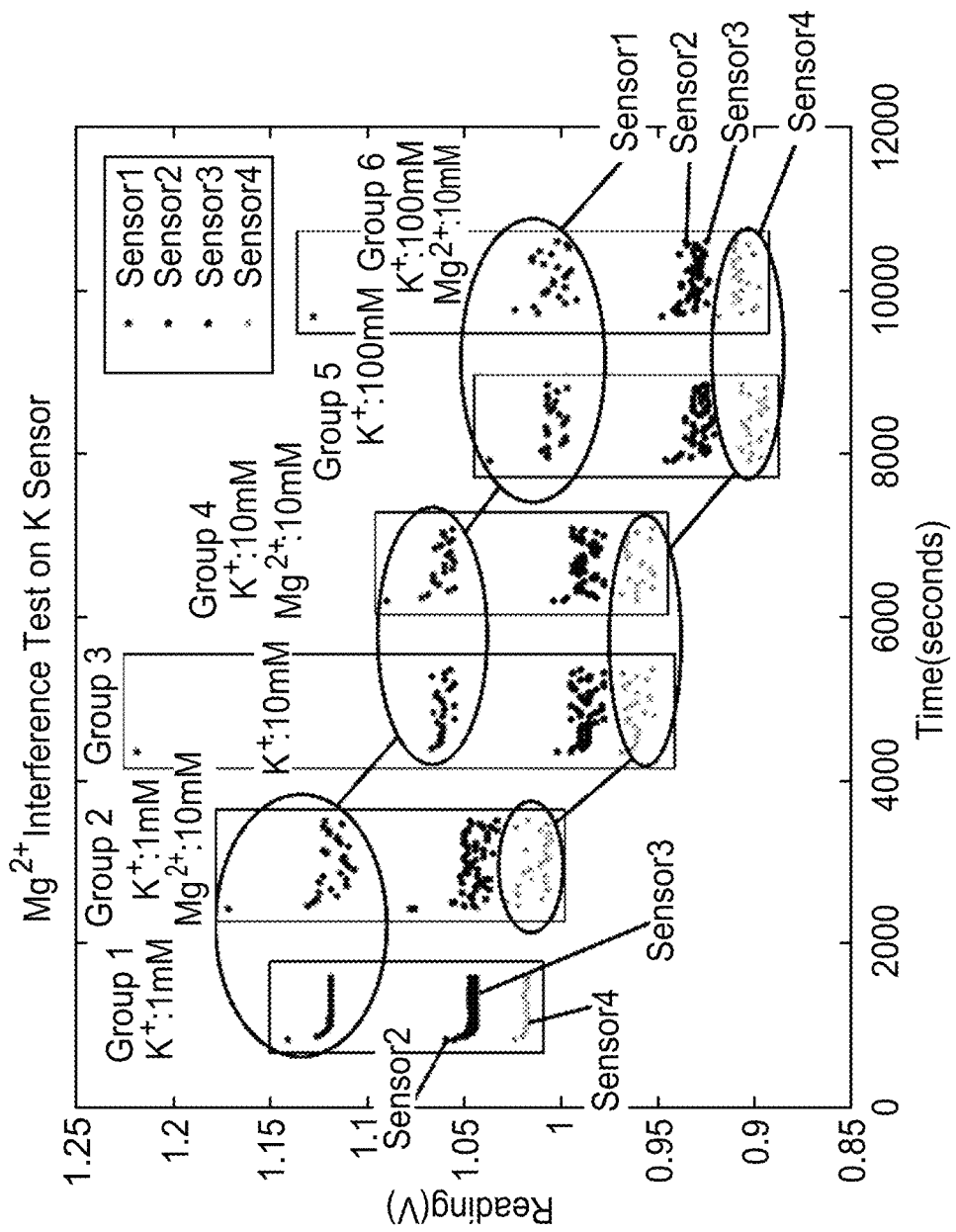
FIG. 29 is a plot showing the effect of magnesium on the performance of potassium sensors, according to an embodiment.

FIG. 29 is a plot showing the effect of magnesium ions ($Mg^{2+}$), as a potential contaminant, on the performance of potassium sensors, according to an embodiment. As shown in FIG. 29, sequential sensor readings (using four distinct sensors, Sensors 1 through 4) for potassium in the presence of magnesium are shown for six different ratios of potassium to magnesium (i.e., Grouping 1=1 mM potassium, 0 mM magnesium; Grouping 2=1 mM potassium, 10 mM magnesium; Grouping 3=10 mM potassium, 0 mM magnesium; Grouping 4=10 mM potassium, 10 mM magnesium; Grouping 5=100 mM potassium, 0 mM magnesium; Grouping 6=100 mM potassium, 10 mM magnesium). The data in FIG. 29 shows that the potassium sensor performance was stable or substantially stable, even in the presence of magnesium.

FIG. 30 is a plot showing the effect of ammonium ($NH_4^+$), as a potential contaminant, on the performance of potassium sensors, according to an embodiment. As shown in FIG. 30, sequential sensor readings (using four distinct sensors, Sensors 1 through 4) for potassium in the presence of ammonium are shown for six different ratios of potassium to magnesium (i.e., Grouping 1=1 mM potassium, 0 mM ammonium; Grouping 2=1 mM potassium, 10 mM ammonium; Grouping 3=10 mM potassium, 0 mM ammonium; Grouping 4=10 mM potassium, 10 mM ammonium; Grouping 5=100 mM potassium, 0 mM ammonium; Grouping 6=100 mM potassium, 10 mM ammonium). The data in FIG. 30 shows that the potassium sensor performance was stable or substantially stable, even in the presence of ammonium.

FIG. 31 is a plot showing a dynamic response of a nitrate sensor to an applied dose of nitrate solution, in accordance with some embodiments. As can be seen in FIG. 31, there is an initial time period (<1,000 seconds) during which the sensor is initially "wetted" with the nitrate-containing solution and detects a rapidly increasing amount of nitrate. After this initial equilibration period, the sensor reaches and maintains a steady-state detected level of nitrate.

In some embodiments, one or more components of the sensor assembly (e.g., a first sensor array segment or a second sensor array segment) includes a processor and a memory storing instructions to cause the processor to one or more of: receive signals from one or more sensors of the sensor assembly, analyze signals from one or more sensors of the sensor assembly to detect or calculate a soil parameter, or send signals to one or more remote computing devices, in response to a sensor detection event. Instructions to analyze signals from one or more sensors of the sensor assembly can include calculating a soil parameter based at least in part on calibration data associated with the one or more sensors, and/or based at least in part on a known equilibration period associated with the one or more sensors.

Sensors, sensor assemblies and/or sensor blocks of the present disclosure can be configured to interface with (e.g., send data to and/or receive data from) one or more automated irrigation systems, drone inspection systems, and/or other agricultural technology systems, for example to cause a modification to a setting (e.g., relating to temperature, irrigation, etc.) or to trigger an alarm (e.g., for presentation to a user via a graphical user interface of a mobile or desktop computing device).

In some embodiments, an apparatus includes a housing and multiple sensor array segments. The multiple sensor array segments include a first sensor array segment and a second sensor array segment. The first sensor array segment can include an antenna, an air temperature sensor, a humidity sensor, and a light sensor. The second sensor array segment can include a soil temperature sensor, an EC sensor, a moisture sensor, an ISFET-based pH sensor, and an array of ISFET-based sensors featuring ruggedized, single-layer or multi-layer membranes for the selective detection of one or a combination of the following soil nutrients: ammonium, calcium, carbonate, chloride, nitrate, phosphate, potassium, sodium, and sulfate, during use and substantially in real time, in an adjacent region of soil. One or both of the first sensor array segment and the second sensor array segment can be disposed within the housing. The apparatus also includes a reference electrode electrically coupled to each of the first sensor array segment and the second sensor array segment. The first sensor array segment can be disposed on a first side of the second sensor array segment, and the reference electrode can be disposed on a second side of the second sensor array segment, the second side of the second sensor array segment opposite the first side of the second sensor array segment.

In some embodiments, the apparatus further includes a third sensor array segment. The third sensor array segment can include a soil temperature sensor, an EC sensor, a moisture sensor, an ISFET-based pH sensor, and an array of ISFET-based sensors featuring ruggedized, single- or multi-layer membranes for the selective detection of one or a combination of the following soil nutrients: ammonium, calcium, carbonate, chloride, nitrate, phosphate, potassium, sodium, and sulfate, during use and substantially in real time, in an adjacent region of soil. The second sensor array segment and the third sensor array segment can be arranged sequentially, in any order, within the housing.

In some embodiments, the apparatus further includes a third sensor array segment and a fourth sensor array segment. One or both of the third sensor array and the fourth sensor array can include a soil temperature sensor, an EC sensor, a moisture sensor, an ISFET-based pH sensor, and an array of ISFET-based sensors featuring ruggedized, single-layer or multi-layer membranes for the selective detection of one or a combination of the following soil nutrients: ammonium, calcium, carbonate, chloride, nitrate, phosphate, potassium, sodium, and sulfate, during use and substantially in real time, in an adjacent region of soil. The second sensor array segment, the third sensor array segment, and the fourth sensor array segment can be arranged sequentially, in any order, within the housing.

In some embodiments, the apparatus is configured such that, in use, the detection of pH by the ISFET pH sensor, the detection of nitrate by the ISFET nitrate sensor, and the detection of other soil nutrients, such as ammonium, calcium, carbonate, chloride, phosphate, potassium, sodium, and sulfate, are performed sequentially.

In some embodiments, an apparatus includes a housing and an ISFET pH sensor disposed within the housing and configured to detect, during use and substantially in real time, pH in an adjacent region of soil. The apparatus also includes an ISFET nitrate sensor, disposed within the housing, configured to detect, during use and substantially in real time, nitrates in an adjacent region of soil. The apparatus also includes at least one of: an ISFET ammonium sensor disposed within the housing and configured to detect, during use and substantially in real time, ammonium in an adjacent region of soil; an ISFET calcium sensor disposed within the housing and configured to detect, during use and substantially in real time, calcium in an adjacent region of soil; an ISFET carbonate sensor disposed within the housing and configured to detect, during use and substantially in real time, carbonates in an adjacent region of soil; an ISFET chloride sensor disposed within the housing and configured to detect, during use and substantially in real time, chloride in an adjacent region of soil; an ISFET phosphate sensor disposed within the housing and configured to detect, during use and substantially in real time, an ISFET carbonate sensor disposed within the housing and configured to detect, during use and substantially in real time, carbonate in an adjacent region of soil; an ISFET potassium sensor disposed within the housing and configured to detect, during use and substantially in real time, potassium in an adjacent region of soil; an ISFET sodium sensor disposed within the housing and configured to detect, during use and substantially in real time, sodium in an adjacent region of soil; an ISFET sulfate sensor disposed within the housing and configured to detect, during use and substantially in real time, sulfates in an adjacent region of soil; or an ISFET phosphate sensor disposed within the housing and configured to detect, during use and substantially in real time, phosphates in an adjacent region of soil, and a reference electrode electrically coupled to each of the ISFET pH sensor, the ISFET nitrate sensor, and the at least one of the ISFET potassium sensor, the ISFET ammonium sensor, or the ISFET phosphate sensor. At least one of the ISFET nitrate sensor, the ISFET pH sensor, and the ISFET potassium sensor can include a fluoropolysiloxane membrane. The apparatus can be configured such that, in use, the detection of nitrate by the ISFET nitrate sensor, the detection of pH by the ISFET pH sensor, and at least one of the detection of potassium by the ISFET potassium sensor, the detection of ammonium by the ISFET ammonium sensor, or the detection of phosphate by the ISFET phosphate sensor, are performed sequentially.

In some embodiments, an apparatus includes a housing, a first sensor array segment, a second sensor array segment, and a reference electrode. The first sensor array segment can include an antenna, an air temperature sensor, a humidity sensor, and a light sensor. The second sensor array segment is disposed within the housing, and includes a soil moisture sensor, an EC sensor, and an ISFET pH sensor configured to detect, during use and substantially in real time, a pH in an adjacent region of soil. The reference electrode is electrically coupled to each of the first sensor array segment and the second sensor array segment. The first sensor array segment is disposed on a first side of the second sensor array segment, and the reference electrode is disposed on a second side of the second sensor array segment, the second side of the second sensor array segment opposite the first side of the second sensor array segment. In some implementations, the apparatus also includes a third sensor array segment. The third sensor array segment can include a soil moisture sensor, an EC sensor, and an ISFET nitrate sensor (e.g., including a fluoropolysiloxane membrane) configured to detect, during use and substantially in real time, nitrates in an adjacent region of soil. Alternatively, or in addition, the third sensor array segment can include a soil moisture sensor, an EC sensor, and an ISFET ammonium sensor (e.g., including a fluoropolysiloxane membrane) configured to detect, during use and substantially in real time, ammonium in an adjacent region of soil. Alternatively, or in addition, the third sensor array segment can include a soil moisture sensor, an EC sensor, and an ISFET phosphate sensor (e.g., including a fluoropolysiloxane membrane) configured to detect, during use and substantially in real time, phosphates in an adjacent region of soil. Alternatively, or in addition, the third sensor array segment can include a soil moisture sensor, an EC sensor, and an ISFET potassium sensor (e.g., including a fluoropolysiloxane membrane) configured to detect, during use and substantially in real time, potassium in an adjacent region of soil.

In some embodiments, an apparatus includes a housing, a first sensor array segment, a second sensor array segment, and a single/common ("shared") reference electrode. The first sensor array segment includes an antenna, an air temperature sensor, a humidity sensor, and a light sensor. The second sensor array segment includes a soil moisture sensor, an EC sensor, and an SFET nitrate sensor (e.g., including a fluoropolysiloxane membrane) configured to detect, during use and substantially in real time, a nitrate in an adjacent region of soil. The reference electrode is electrically coupled to each of the first sensor array segment and the second sensor array segment. One or more of the first sensor array segment, the second sensor array segment, or the reference electrode is at least partially disposed within the housing. The first sensor array segment can be disposed on a first side of the second sensor array segment, and the reference electrode can be disposed on a second side of the second sensor array segment, the second side of the second sensor array segment opposite the first side of the second sensor array segment.

In some embodiments, an apparatus includes a housing, a first sensor array segment, a second sensor array segment, and a reference electrode. The first sensor array segment includes an antenna, an air temperature sensor, a humidity sensor, and a light sensor. The second sensor array segment is disposed within the housing, and includes a soil moisture sensor, an EC sensor, and an ISFET ammonium sensor configured to detect, during use and substantially in real time, ammonium in an adjacent region of soil. The reference electrode is electrically coupled to each of the first sensor array segment and the second sensor array segment. The first sensor array segment is disposed on a first side of the second sensor array segment, and the reference electrode is disposed on a second side of the second sensor array segment, opposite the first side of the second sensor array segment.

In some embodiments, an apparatus includes a housing, a first sensor array segment, a second sensor array segment, and a reference electrode. The first sensor array segment includes an antenna, an air temperature sensor, a humidity sensor, and a light sensor. The second sensor array segment disposed within the housing, the second sensor array segment including a soil moisture sensor, an EC sensor, and an ISFET phosphate sensor configured to detect, during use and substantially in real time, phosphates in an adjacent region of soil. The reference electrode is electrically coupled to each of the first sensor array segment and the second sensor array segment. The first sensor array segment is disposed on a first side of the second sensor array segment, and the reference electrode is disposed on a second side of the second sensor array segment, opposite the first side of the second sensor array segment.

In some embodiments, the ISFET phosphate sensor can include a first, ISFET low-pH phosphate sensor, the second sensor array segment further including a second, ISFET high-pH phosphate sensor.

In some embodiments, an apparatus includes a housing, a first sensor array segment, a second sensor array segment, and a reference electrode. The first sensor array segment includes an antenna, an air temperature sensor, a humidity sensor, and a light sensor. The second sensor array segment can be disposed within the housing, the second sensor array segment including a soil moisture sensor, an EC sensor, and a ISFET potassium sensor (e.g., including a fluoropolysiloxane membrane) configured to detect, during use and substantially in real time, potassium in an adjacent region of soil. The reference electrode can be electrically coupled to each of the first sensor array segment and the second sensor array segment. The first sensor array segment can be disposed on a first side of the second sensor array segment, and the reference electrode is disposed on a second side of the second sensor array segment, opposite the first side of the second sensor array segment.

As used herein, the terms "about" and "approximately" generally mean plus or minus 10% of the value stated, for example about 250 µm would include 225 µm to 275 µm, about 1,000 µm would include 900 µm to 1,100 µm.

While various embodiments of the system, methods and devices have been described above, it should be understood that they have been presented by way of example only, and not limitation. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. An apparatus, comprising:
a housing;
a plurality of sensor array segments, including:
a first sensor array segment including wireless communication hardware, the wireless communication hardware including an antenna; and
a second sensor array segment disposed within the housing, comprising:
a soil temperature sensor,
an electrical conductivity (EC) sensor,
a moisture sensor,
an ion-sensitive field effect transistor (ISFET) nitrate sensor configured to detect nitrates in an adjacent region of soil,
a first ISFET phosphate sensor configured to detect phosphates in a pH range of 2-7,
a second ISFET phosphate sensor configured to detect phosphates in a pH range of 7-12,
an ISFET potassium sensor configured to detect, during use, potassium in an adjacent region of soil, and
an ISFET pH sensor configured to detect, during use, pH in an adjacent region of soil; and
a reference electrode electrically coupled to each of the first sensor array segment and the second sensor array segment,
the first sensor array segment disposed on a first side of the second sensor array segment, and
the reference electrode disposed on a second side of the second sensor array segment, the second side of the second sensor array segment opposite the first side of the second sensor array segment.

2. The apparatus of claim 1, wherein the second sensor array segment further comprises an ISFET ammonium sensor configured to detect, during use, ammonium in an adjacent region of soil.

3. The apparatus of claim 1, further comprising a third sensor array segment including:
a soil temperature sensor,
an EC sensor,
a moisture sensor,
an ISFET nitrate sensor configured to detect, during use, nitrates in an adjacent region of soil,
at least one ISFET phosphate sensor configured to detect, during use, phosphates in an adjacent region of soil, an ISFET potassium sensor configured to detect, during use, potassium in an adjacent region of soil, and an ISFET pH sensor configured to detect, during use, pH in an adjacent region of soil, the second sensor array segment and the third sensor array segment arranged sequentially, in any order, within the housing.

4. The apparatus of claim 1, further comprising a third sensor array segment and a fourth sensor array segment, each of the third sensor array and the fourth sensor array including:

a soil temperature sensor, an EC sensor, a moisture sensor, an ISFET nitrate sensor configured to detect, during use, nitrates in an adjacent region of soil, at least one ISFET phosphate sensor configured to detect, during use, phosphates in an adjacent region of soil, an ISFET potassium sensor configured to detect, during use, potassium in an adjacent region of soil, and an ISFET pH sensor configured to detect, during use, pH in an adjacent region of soil, the second sensor array segment, the third sensor array segment, and the fourth sensor array segment arranged sequentially, in any order, within the housing.

5. The apparatus of claim 1, configured such that, in use, the detection of nitrate by the ISFET nitrate sensor, the detection of pH by the ISFET pH sensor, and at least one of the detection of potassium by the ISFET potassium sensor, the detection of ammonium by the ISFET ammonium sensor, or the detection of phosphate by the ISFET phosphate sensor, are performed sequentially.

6. An apparatus, comprising:

a housing;

a first sensor array segment, including an antenna;

a second sensor array segment disposed within the housing, the second sensor array segment including:

a soil moisture sensor, an electrical conductivity (EC) sensor, an ion-sensitive field-effect transistor (ISFET) pH sensor configured to detect, during use and in an adjacent region of soil, a pH, a first ISFET phosphate sensor configured to detect phosphates in a pH range of 2-7, and a second ISFET phosphate sensor configured to detect phosphates in a pH range of 7-12; and a reference electrode electrically coupled to each of the first sensor array segment and the second sensor array segment, the first sensor array segment disposed on a first side of the second sensor array segment, and the reference electrode disposed on a second side of the second sensor array segment, the second side of the second sensor array segment opposite the first side of the second sensor array segment.

7. The apparatus of claim 6, wherein the ISFET pH sensor includes a fluoropolysiloxane membrane.

8. The apparatus of claim 6, further comprising a third sensor array segment including a soil moisture sensor, an EC sensor, and an ISFET nitrate sensor configured to detect, during use, nitrates in an adjacent region of soil.

9. The apparatus of claim 6, further comprising a third sensor array segment including a soil moisture sensor, an EC sensor, and an ISFET ammonium sensor configured to detect, during use, ammonium in an adjacent region of soil.

10. The apparatus of claim 6, further comprising a third sensor array segment including a soil moisture sensor, an EC sensor, and an ISFET phosphate sensor configured to detect, during use, phosphates in an adjacent region of soil.

11. The apparatus of claim 6, further comprising a third sensor array segment including a soil moisture sensor, an EC sensor, and an ISFET potassium sensor configured to detect, during use, potassium in an adjacent region of soil.

* * * * *